United States Patent
Katashiro et al.

(10) Patent No.: US 6,545,260 B1
(45) Date of Patent: Apr. 8, 2003

(54) LIGHT SCANNING OPTICAL DEVICE WHICH ACQUIRES A HIGH RESOLUTION TWO-DIMENSIONAL IMAGE WITHOUT EMPLOYING A CHARGE-COUPLED DEVICE

(75) Inventors: Masahiro Katashiro, Okaya (JP); Kazuya Matsumoto, Kamiina-gun (JP); Shuichi Takayama, Hachioji (JP); Katsuya Ono, Hino (JP); Takeshi Suga, Sagamihara (JP); Hiroyuki Sangu, Akishima (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/713,954

(22) Filed: Nov. 16, 2000

(30) Foreign Application Priority Data

Nov. 19, 1999 (JP) .............................. 11-330191
Nov. 19, 1999 (JP) .............................. 11-330193

(51) Int. Cl.⁷ ................................. G01B 9/10
(52) U.S. Cl. ................ 250/227.26; 250/234; 359/196; 359/202
(58) Field of Search .............. 250/227.11, 227.12, 250/227.2, 234, 230, 227.26; 359/201, 202, 212, 196, 198, 199, 213, 223, 726, 727, 728, 368, 385

(56) References Cited

U.S. PATENT DOCUMENTS

| 4,938,205 A | 7/1990 | Nudelman |
| 5,045,936 A | 9/1991 | Lobb et al. |
| 5,120,953 A | 6/1992 | Harris |
| 5,161,053 A | 11/1992 | Dabbs |
| 5,323,009 A * | 6/1994 | Harris ................. 250/227.2 |
| 5,467,767 A * | 11/1995 | Alfano et al. ............. 600/476 |
| 5,742,419 A | 4/1998 | Dickensheets et al. |
| 5,907,425 A | 5/1999 | Dickensheets et al. |
| 6,057,952 A | 5/2000 | Kubo et al. |
| 6,172,789 B1 * | 1/2001 | Kino et al. ............... 359/198 |

FOREIGN PATENT DOCUMENTS

| JP | 4-38092 | 2/1992 |
| JP | 6-79110 | 10/1994 |
| JP | 7-299026 | 11/1995 |
| WO | WO 95/25971 | 3/1994 |

* cited by examiner

Primary Examiner—Stephone B. Allen
Assistant Examiner—Bradford Hill
(74) Attorney, Agent, or Firm—Frishauf, Holtz, Goodman & Chick, P.C.

(57) ABSTRACT

A light scanning optical device comprises a light source for entirely illuminating a subject, a converging optical system for converging light returning from a specific minute region of the subject, a light detector for detecting the light converged by the converging optical system, and a scanning mirror for scanning the minute region, the scanning mirror being produced by a semiconductor manufacturing process.

31 Claims, 14 Drawing Sheets

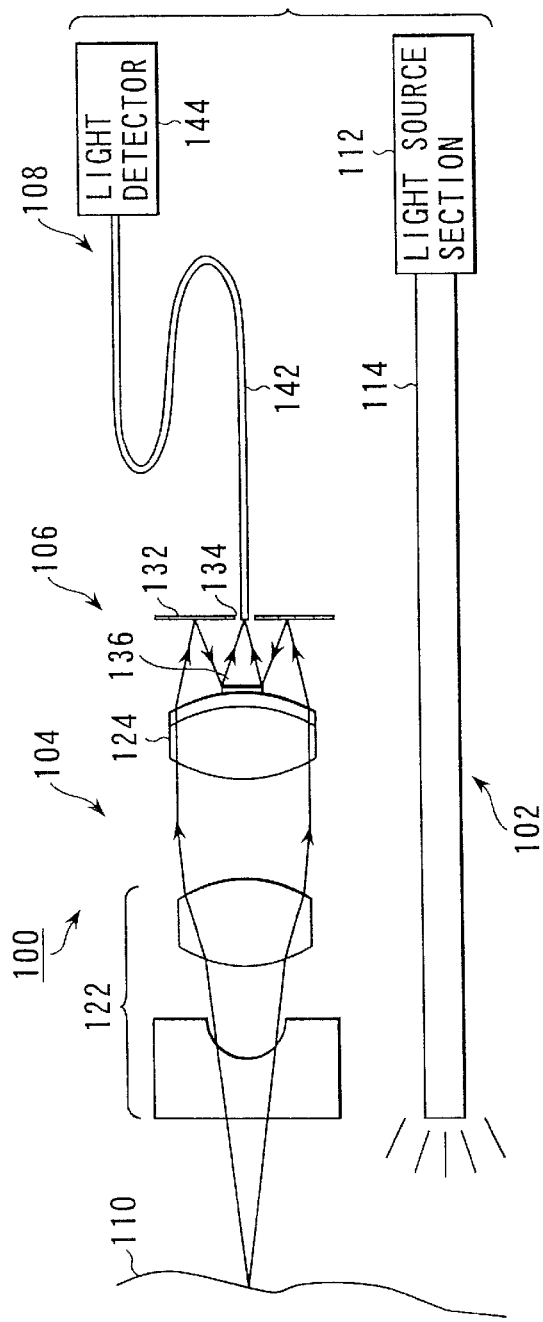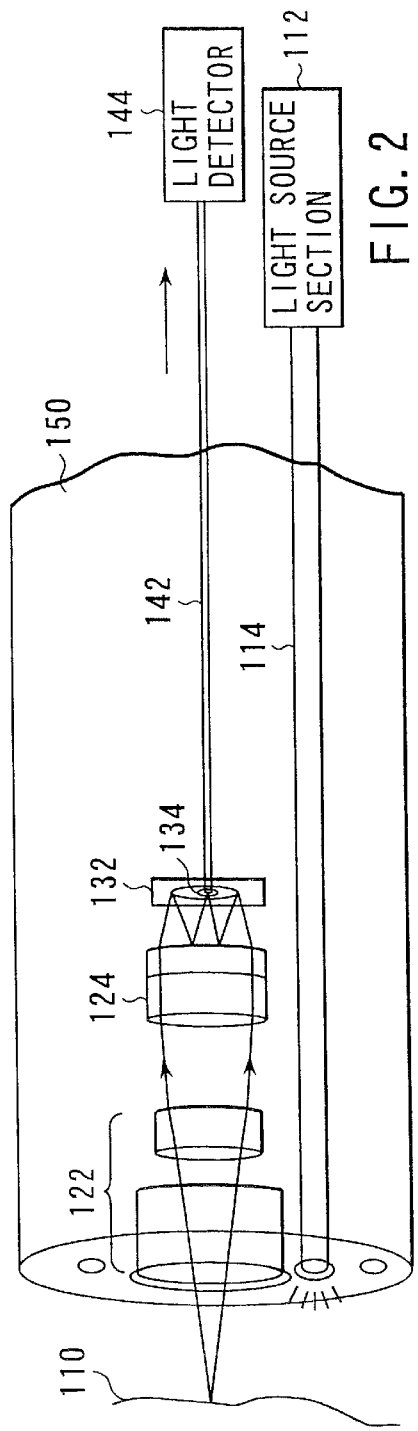

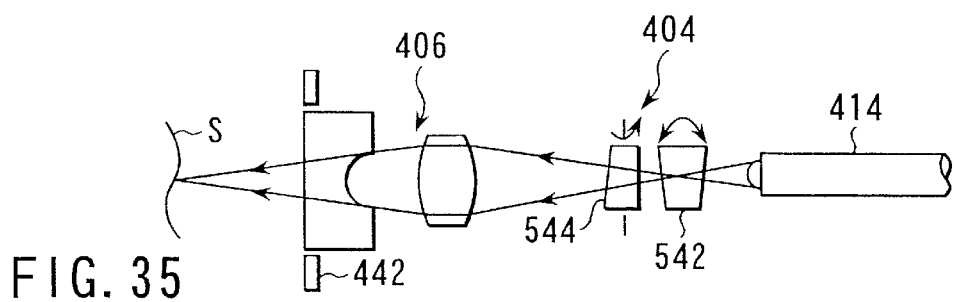
FIG. 35
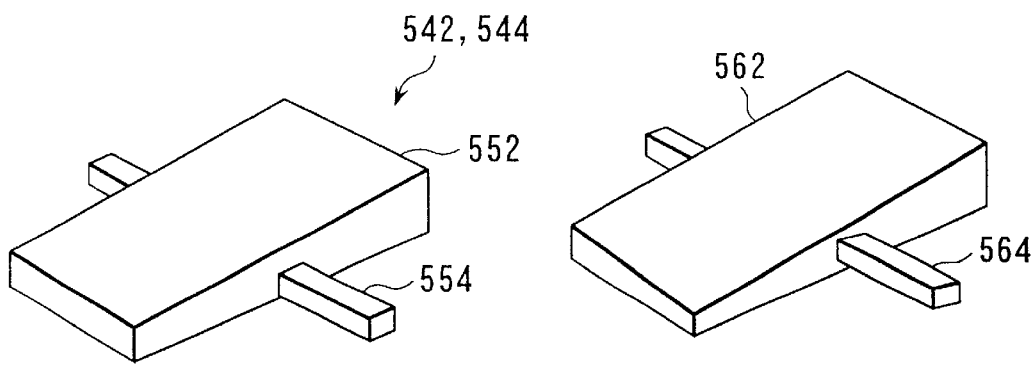
FIG. 36
FIG. 38
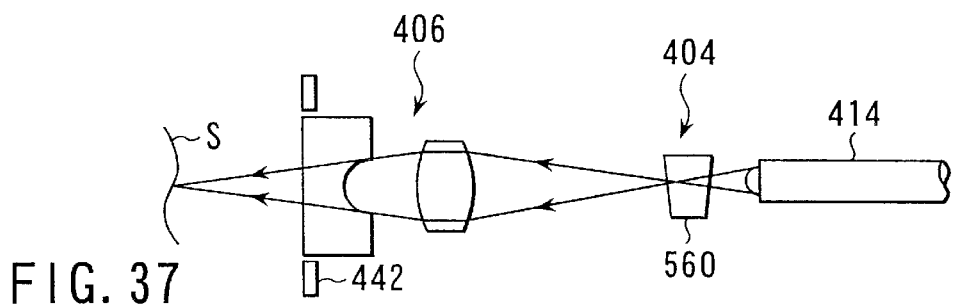
FIG. 37
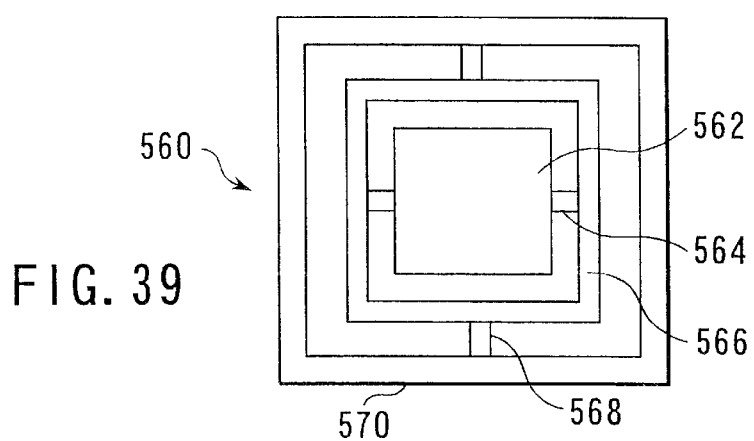
FIG. 39

LIGHT SCANNING OPTICAL DEVICE WHICH ACQUIRES A HIGH RESOLUTION TWO-DIMENSIONAL IMAGE WITHOUT EMPLOYING A CHARGE-COUPLED DEVICE

CROSS-REFERENCE TO RELATED APPLICATIONS

This application is based upon and claims the benefit of priority from the prior Japanese Patent Applications No. 11-330191, filed Nov. 19, 1999; and No. 11-330193, filed Nov. 19, 1999, the entire contents of which are incorporated herein by reference.

BACKGROUND OF THE INVENTION

The present invention relates to a light scanning optical device including a scanning optical system, and an endoscope using the same.

In a conventional electronic endoscope, the illumination light emitted from a light source is guided to a subject by a light guide to illuminate it. The reflected light from the subject passes through an objective lens is imaged by an imaging lens, and is subject to photoelectrical conversion by an image sensor such as a charge coupled device (CCD) disposed on its image plane. A signal from the CCD is imaged by a signal processor, and its image is displayed on a monitor, for example.

The CCD, which is employed in a conventional electronic endoscope, is expensive. In particular, a miniaturized CCD is very expensive because it requires an advanced manufacturing process. This causes an increased cost of an optical device such as, for example, an endoscope.

In addition, there is a restriction that the resolution of an obtained image almost depends on the resolution of the CCD. In the CCD, an image is outputted in units of pixels. With advancement of the manufacturing process, although the size of the pixels becomes about 4 um, it is very difficult to reduce pixel size any more without sacrificing performance such as sensitivity.

However, the resolution of the objective lens can be increased to about 1 um depending on use. That is, the conventional electronic endoscope cannot take advantage of the high resolution possessed by an optical system, thus making it difficult to achieve high resolution.

BRIEF SUMMARY OF THE INVENTION

The present invention has been made in view of such circumstance. It is an object of the present invention to provide an optical device and an endoscope using the same which is capable of acquiring a two-dimensional image with high resolution without employing an expensive CCD.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrates presently preferred embodiments of the invention, and together with the general description given above and the detailed description of the preferred embodiments given below, serves to explain the principle of the invention.

FIG. 1 schematically shows a light scanning optical device according to a first embodiment of the present invention;

FIG. 2 schematically shows an endoscope having the light scanning optical device shown in FIG. 1 incorporated therein;

FIG. 35 schematically shows a light scanning optical device as a seventh modification of the light scanning optical device according to the second embodiment of the present invention;

FIG. 36 is a partial perspective view of a one-dimensional scanning prism shown in FIG. 35;

FIG. 37 schematically shows a light scanning optical device as an eighth modification of the light scanning optical device according to the second embodiment of the present invention;

FIG. 38 is a partial perspective view of a two-dimensional scanning prism shown in FIG. 37;

FIG. 39 is a plan view of a two-dimensional scanning prism shown in FIG. 37;

DETAILED DESCRIPTION OF THE INVENTION

Figure 3:
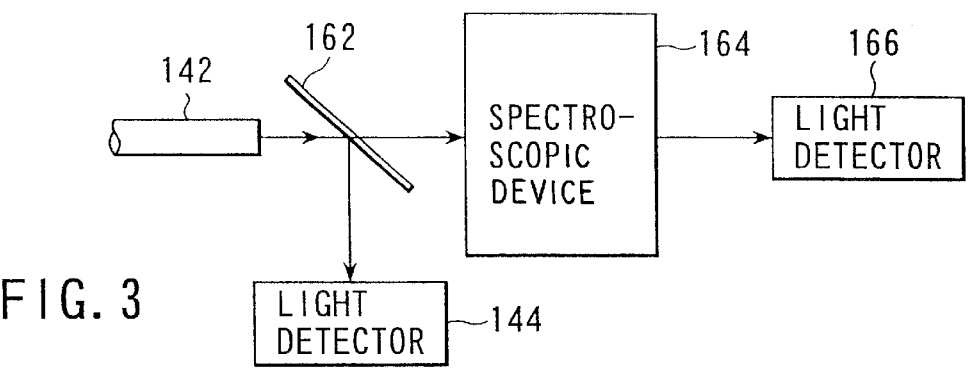
FIG. 3 schematically shows a light detecting section at the light scanning optical device as a first modification of the light scanning optical device according to the first embodiment of the present invention.

As shown in FIG. 1, a light scanning optical device 100 according to a first embodiment of the present invention comprises: an illuminating unit 102 for entirely illuminating a subject 100; a converging optical system 104 for converging a return light from a specific minute region of the subject 110; a light detecting section 108 for detecting the return light focused by the converging optical system; and a scanning section 106 for scanning the aforementioned minute region.

The illuminating unit 102 comprises: a light source section 112 for generating illumination light; and a light guide 114 for guiding the illumination light from the light source section 112, thereby illuminating the light to the subject 110. The light source section 112 sequentially emits colored lights such as red, green and blue (RGB).

The converging optical system 104 comprises an objective lens 122 facing the subject 110 and an imaging lens 124 for imaging the return light that passes through the objective lens 122.

The scanning section 106 comprises: a first reflection mirror 132 for returning an optical path for the return light from the imaging lens 124; and a second reflection mirror 136 for returning again the optical path for the return light reflected by the first reflection mirror 132. The first reflection mirror 132 and the second reflection mirror 136 cross an optical axis of the imaging lens 124 together. Therefore, the objective lens 122, imaging lens 124, first reflection mirror 132, and second reflection mirror 136 are linearly arranged each other. Such layout is advantageous in reducing the optical device 100 in diameter.

The first reflection mirror 132 has a reflection face swingable in a two-dimensional manner, and the reflection face has at its center an opening 134, which allows the return light to pass through. The first reflection mirror 132 has a reflection face, which can be swung around two axes crossing each other, and more preferably perpendicular to each other. Since the first reflection mirror 132 has the reflection face that enables two-dimensional scanning, the mirror is also referred, herein, as a two-dimensional mirror or merely a scanning mirror.

Such scanning mirror 132 is a gimbal type scanning mirror, for example, which is a micro-machine mirror produced by employing a semiconductor manufacturing process. This semiconductor manufacturing process enables processing in order of $\mu$m, and a micro-machine mirror produced in this process is very small. This contributes to device miniaturization. The micro-machine manufacturing process is operated under very generous rules compared with a process for manufacturing a CCD. Thus, the micromachine mirror can be manufactured more inexpensively than the CCD. The scanning mirror 132 is driven by an electrostatic system, for example. The scanning mirror 132 may be driven by an electromagnetic system or a piezoelectric system.

The second reflection mirror 136 is supported by the imaging lens 124, and has a reflection face positioned at the center of the imaging lens 124. The second reflection mirror 136 is produced by selectively vapor-depositing a metal on the optical surface of the imaging lens 124, for example. Here, the second reflection mirror 136 is referred to as a fixed mirror as oppose to the scanning mirror 132.

The light detecting section 108 comprises: a light guide 142 having an end face disposed on the image plane of the converging optical system 104; and a light detector 144 for converting into an electrical signal the return light received from the light guide 142.

The light guide 142 allows the light detector 144 to be disposed apart from the converging optical system 104 and the scanning section 106, thereby enhancing the degree of freedom of the device configuration.

The light guide 142 is a multiple mode fiber, for example. The light guide 142 may be a fiber bundle or an optical fiber amplifier. The optical fiber amplifier amplifies light, and thus, is advantageous in eliminating the shortage of light quantity of the return light from the subject.

The light detector 144 is a photo-multiplier, for example. The light detector 144 may be a photodiode, Avalanche photodiode, or pin photodiode. The photo-multiplier or Avalanche photodiode has a light amplification action, and thus, is advantageous in eliminating the shortage of light quantity of the return light from the subject.

In FIG. 1, the illumination light produced by the light source section 112, for example, sequentially emitted colored lights such as RGB, which propagates inside of the light guide 114, is projected from the end face of the light guide 114 to illuminate the subject 110.

The return light reflected or scattered by the subject 110 that exists in a specific minute region conjugate to the end face of the light guide 142 passes through the objective lens 122 to be converted into convergent light by the imaging lens 124. The convergent light is reflected by the scanning mirror 132, and then, is reflected by the fixed mirror 136. Thereafter, the reflected light passes through the opening 134, and arrives at the end face of the light guide 142.

The light incident to the light guide 142 propagates its inside, reaches the light detector 144, and is converted to an electrical signal corresponding to its intensity by the light detector 144.

The two-dimensional scanning mirror 132 can change the orientation of its reflection face arbitrarily in a two-dimensional manner as required. A change in orientation of the reflection face of the scanning mirror 132 moves or scans the minute region conjugate to the end face of the light guide 142. That is, the minute region is scanned according to the change in orientation of the reflection face of the scanning mirror 132. If the subject 100 exists on the scanning plane, the reflected or scattered light at a portion of the subject corresponding to the minute region is detected by the light detector 144.

Therefore, while the minute region is scanned in a two-dimensional manner by the two-dimensional scanning mirror 132, the reflected or scattered light from the minute region is detected by the light detector. Then, the detected light is processed together with a scanning signal and detecting signal, whereby an image within the scanning range of the subject 110 is obtained. In particular, with respect to the illumination unit 102 that sequentially projects the colored lights such as RGB, similar processing is performed for each of these lights, whereby a color image within the scanning range of the subject 110 is obtained.

The resolution of the thus obtained image depends on the size of the minute region conjugate to the end face of light guide 142. This depends on the numerical aperture of the end face of the light guide 142 and a magnification of the converging optical system 104. In other words, the size of an image of the end face of the light guide 142 formed by the light connecting optical system 104 corresponds to the resolution of the light scanning optical device. The light connecting optical system 104 can form an image of the end face of the light guide 142 as an image of 1 $\mu$m or less in diameter. Therefore, this scanning optical device can achieve the resolution of 1 $\mu$m.

In observation of the subject 110, a true-zoom like observation may be performed. That is, at the beginning of the observation, the scanning range of the gimbal type scanning mirror is set to be relatively large, whereby an entire image is grasped within the observation range of the subject. Then, by narrowing the scanning range, a portion to be observed in particular detail may be observed with high sensitivity and at a high speed in detail.

As understood from the above description, the light scanning optical device according to the first embodiment can achieve an image of the subject with high resolution without employing a CCD, which is relatively expensive.

Such light scanning optical device 100 is applied to an endoscope 150, for example, as shown in FIG. 2. This endoscope 150 comprises a light scanning optical device 100 (other than the light detector 144 and the light source section 112) at the distal end of its insert section.

The light guide 114 of the illumination unit 102 extends the inside of a channel formed inside of the endoscope 150, and its end face is positioned at a distal end face of the endoscope 150. The objective lens 122, imaging lens 124, first reflection mirror 132, and second reflection mirror are disposed inside of a inflexible portion of the endoscope 150 all together, and an optical surface of the objective lens 122 is exposed to the distal end face of the endoscope 150. In addition, although not shown, the endoscope 150 includes forceps channels for various treatments.

A viewing direction of the light scanning optical device 100 incorporated in the endoscope 150 coincides with the insert direction of the endoscope 150. Therefore, the endoscope 150 is a so-called straightforward viewing type endoscope in which the insert direction and viewing direction coincide with each other, which is very preferable in operability.

Using the micro-machine mirror 132 as a scanning mirror contributes to reducing the light scanning optical device 100 in diameter, and allows the light scanning optical device 100 to be preferably incorporated in the distal end of the endoscope 150. In addition, the first reflection mirror 132 and the second reflection mirror 136, which fold back the return light from the subject 110, contributes to reduce the physical length of an optical system, so as to allow the endoscope 150 to have a short inflexible portion.

The light scanning optical device according to the present invention is not limited to the aforementioned first embodiment, and various modifications or changes may be made without departing from the scope of the invention.

In a first modification of the light scanning optical device according to the first embodiment, as shown in FIG. 3, the light detecting section 108 comprises: a light guide 142; a beam splitter 162 for splitting a light beam projected from the light guide 142 into two light beams; a light detector 144 for detecting one of the divided light beams; a spectroscopic device 164 for spectroscopically dispersing the other divided light beam; and a light detector 166 for detecting the spectroscopically dispersed light. The spectroscopic device 164 is a spectroscope, for example. The spectroscopic device 164 may be a diffraction lattice or a prism.

The beam of return light from the specific minute region of the subject 110, which is projected from the light guide 142, is divided into two beams by the beam splitter 162. One beam directly reaches the light detector 144, and is subject to photoelectrical conversion. The other beam reaches the light detector through the spectroscopic device 164, and is thus subject to photoelectrical conversion.

According to the light scanning optical device according to this modification, light of a desired wavelength is selected by the spectroscopic device 164, whereby, for example, fluorescence specific to a lesion is detected, and its fluorescence image is obtained. Namely, according to the light scanning optical device according to this modification, fluorescence observation as well as general observation is performed. The lesion may emit specific fluorescence, making it possible to diagnose lesion based on fluorescence observation.

Figure 4:
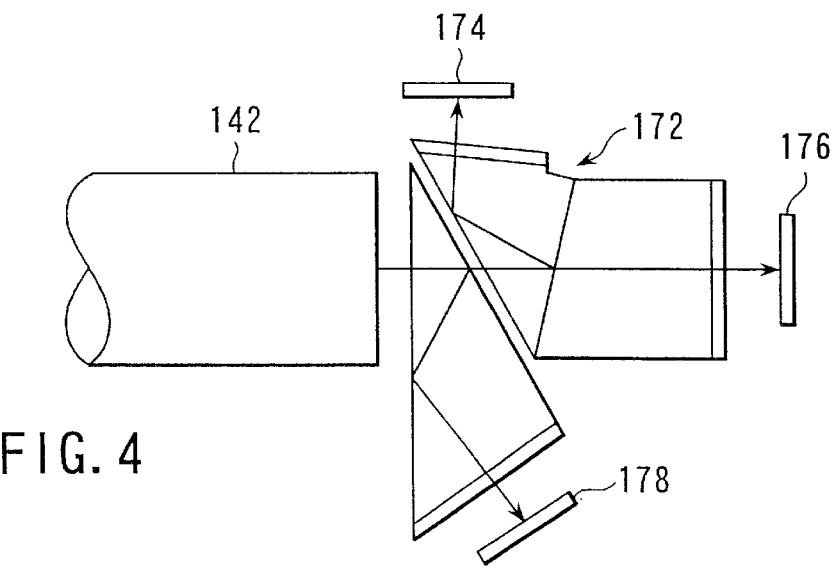
FIG. 4 schematically shows a light detecting section at a light scanning optical device as a second modification of the light scanning optical device according to the first embodiment of the present invention.

In a second modification of the light scanning optical device according to the first embodiment, the light source section 112 of the illumination unit 102 emits white color light. As shown in FIG. 4, the light detecting section 108 comprises: the light guide 142; a color decomposing prism 172 for splitting the light beam projected from the light guide 142 into three light beams corresponding to RGB; a red color light detector 174 for detecting red color light; a green color light detector 176 for detecting green color light; and a blue color light detector 178 for detecting blue color light.

The beam of return light from the specific minute region of the subject 110, which is projected from the light guide 142, is divided into three beams of red color light, green color light, and blue color light corresponding to RGB by the color decomposing prism 172. The divided beams of red color light, green color light, and blue color light reach the red color light detector 174, green color light detector 176, and blue color light detector 178, respectively, and are thus subject to photoelectrical conversion.

Since the light scanning optical device according to this modification obtains an RGB signal through one scanning of the subject, it has higher dynamic resolution than a device that acquires an image by sequentially projecting the colored lights such as RGB.

Figure 5:
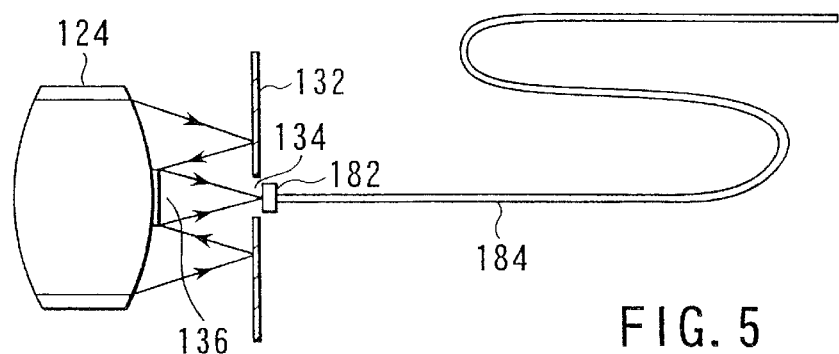
FIG. 5 schematically shows a light detecting section at a light scanning optical device as a third modification of the light scanning optical device according to the first embodiment of the present invention.

In a third modification of the light scanning optical device according to the first embodiment, as shown in FIG. 5, the light detecting section 108 includes a light detector 182 disposed at the image plane of the imaging lens 124. Although the light detector 182 is a photodiode, for example, it may be a pin photodiode or an Avalanche photodiode.

The light detector 182 may comprise an on-chip converging lens formed integrally on its own detector in order to improve the sensitivity of light detection. The light detector 182 may be formed together with an amplifier or an AD converting circuit in order to improve sensitivity, and the thus amplified signal or digitized signal is acquired.

The light detector 182 may be formed integrally with the scanning mirror 132 by employing a semiconductor micromachine production technique in order to improve precision of positioning of elements and in order to reduce a length of the inflexible portion of the endoscope 150 having the light scanning optical device 100 incorporated therein.

The return light from the specific minute region of the subject 110 is converted into convergent light by the imaging lens 124. The converted light is reflected sequentially by the scanning mirror 132 and the fixed mirror 136. Then, the reflected light, passing through the opening 134 of the scanning mirror 132, directly strikes the light detector 182, and is converted into an electrical signal corresponding to its intensity. The electrical signal outputted from the light detector 182 is taken out via an electrical signal output wire 184.

In response to the illumination unit 102 that projects white color light to the subject 110, the light detector 182 comprises a three-color filter, whereby a color image is produced. In response to the illumination unit 102 that sequentially projects colored lights such as RGB to the subject 110, the image signal of each color outputted from the light detector 182 is composed on a computer, whereby a color image is produced.

Since the light scanning optical device according to the present modification does not have any medium such as a light guide for guiding the light from the subject 110 to the light detector 182, this device is small in light loss, and advantageous in cost reduction.

Figure 6:
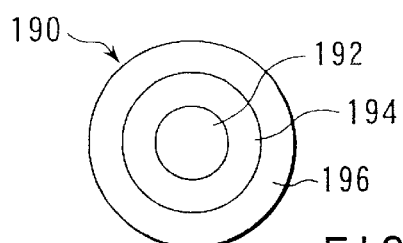
FIG. 6 schematically shows a light detecting section at a light scanning optical device as a fourth modification of the light scanning optical device according to the first embodiment of the present invention.
Figure 7:
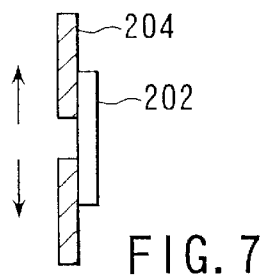
FIG. 7 schematically shows a light detecting section at a light scanning optical device as a fifth modification of the light scanning optical device according to the first embodiment of the present invention.

In a fourth modification of the light scanning optical device according to the first embodiment, the light detecting section 108 includes a light detector 190 disposed on the image plane of the converging optical system 104. As shown in FIG. 6, the light detector 190 comprises: a first photodiode 192 of circular shape positioned at the center; a second photodiode 194 of ring shape positioned at the periphery of the first photodiode 192; and a third photodiode 196 of ring shape positioned at the periphery of the second photodiode 194.

Output signals of the photodiodes 192, 194, and 196 are selectively processed according to their required resolution or depth of field. For example, in image acquisition, only the output signal of the first photodiode 192 at the center is utilized in response to a request for high resolution. In response to a request for a large depth of field, an output signal of the second photodiode 194 at its outside as well as an output signal of the first photodiode 192 is utilized. In response to a request for a further large depth of field, an output signal of the third photodiode at its further outside is utilized. The number of photodiodes is not limited to three, and may be increased or decreased as required.

In order to obtain a color image, the light detector 190 may have the photodiodes 192, 194, and 196 divided into three fan-shaped portions with equal expansion angles with their center being a reference, and three-color filters corresponding to respective RGB light provided at these divided portions.

In a fifth modification of the light scanning optical device according to the first embodiment, the light detecting section 108 comprises: a light detector 202 disposed on the image plane of the converging optical system 104; and a stop 204 for varying a light receiving region at the light detector 202. The stop 204 is a mechanical stop that can change a diameter of an opening mechanically, for example. The stop 204 may be a liquid crystal stop that can change a rate of transmission electrically.

Expansion of the light receiving region of the light detector 202 caused by the stop 204 degrades resolution, but increases the depth of field. Conversely, reduction of the light receiving region of the light detector 202 caused by the stop 204 decreases the depth of field, but improves resolution. Therefore, the stop 204 is adjusted according to required resolution or depth of field.

Figure 8:
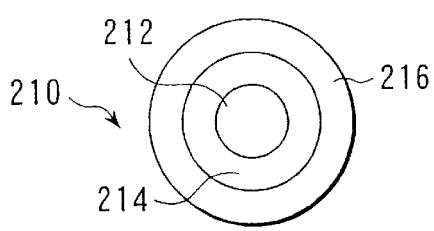
FIG. 8 shows an end face of a light guide of a light detecting section at a light scanning optical device as a sixth modification of the light scanning optical device according to the first embodiment of the present invention.
Figure 9:
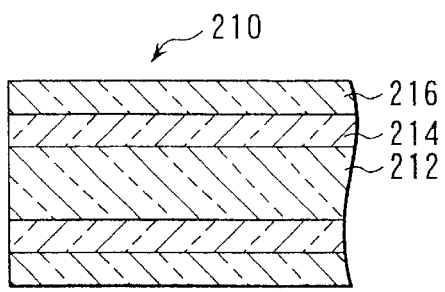
FIG. 9 shows a longitudinal section of the light guide shown in FIG. 8.

In a sixth modification of the light scanning optical device according to the first embodiment, the light detecting section 108 comprises: a light guide 210 having its end face disposed on the image plane of the converging optical system 104; and a light detector 190 described by referring to FIG. 6. As shown in FIGS. 8 and 9, the light guide 210 comprises: a first light guide portion 212 of circular shape positioned at the center; a second light guide portion 214 of ring shape positioned at the periphery of the first light guide portion 212; and a third light guide portion 216 of ring shape further positioned at the periphery of the second light guide portion 214. The light guide 210 may comprise one fiber or a fiber bundle.

The first, second, and third light guide portions 212, 214, and 216 allow light to travel to the first, second, and third photodiodes 192, 194, and 196 of the light detector 190, respectively.

Output signals of the photodiodes 192, 194, and 196 are selectively utilized for image processing according to their required resolution or depth of field. For example, only the output signal of the first photodiode 192 is utilized in response to a request for high resolution. In addition, the output signals of all the photodiodes 192, 194, and 196 are utilized in response to a request for large depth of field.

In order to obtain a color image, the light detector 190 may have the photodiodes 192, 194, and 196 divided into three fan-shaped portions with equal expansion angles with their center being a reference, and three-color filters corresponding to RGB light provided at these divided portions.

Figure 10:
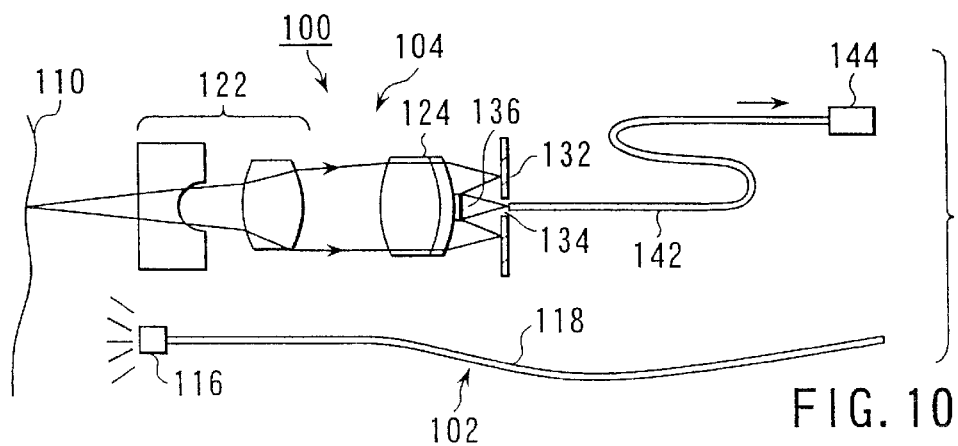
FIG. 10 schematically shows a light scanning optical device as a seventh modification of the light scanning optical device according to the first embodiment of the present invention.

In a seventh modification of the light scanning optical device according to the first embodiment, as shown in FIG. 10, the illumination unit 102 comprises a solid light emitting element 116 disposed near the objective lens 122. This solid light emitting element 116 is driven in accordance with a signal supplied via an input wire 118.

The solid light emitting element 116 is a VSCEL (vertical cavity surface emitting laser), for example. The solid light emitting element 116 may be a general end face light emitting laser, an LED (light emitting diode), an SLD (super luminescent diode), an EL (electroluminescent device), or a PDP (plasma display panel). The solid light emitting element 116 may have an on-chip converging lens formed integrally with the element itself.

In a light scanning optical device of such type in which a color image of one screen is produced by one scan of the scanning mirror 132, the solid light emitting element 116 emits white color light or three RGB-color lights at a predetermined intensity with time. On the other hand, in the device of such type in which the light scanning optical device acquires an image of one screen for each of the colors RGB through three scans of the scanning mirror 132, and composes the image of each color to produce a color image, the solid light emitting element 116 sequentially emits the three RGB colors in time series.

Since the light scanning optical device 100 according to the present modification has no medium such as a fiber for guiding illumination light, it is advantageous in miniaturization and price reduction of the entire device.

Figure 11:
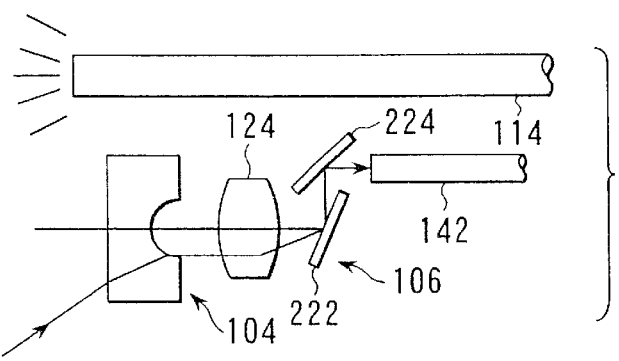
FIG. 11 schematically shows a light scanning optical device as an eighth modification of the light scanning optical device according to the first embodiment of the present invention.

In an eighth modification of the light scanning optical device according to the first embodiment, as shown in FIG. 11, a scanning section 106 comprises: a first reflection mirror 222 for folding an optical path of the return light from the imaging lens 124; and a second reflection mirror 224 for folding again the optical path of the return light from the imaging lens 222. The first reflection mirror 222 crosses an optical axis of the imaging lens 124, and the second reflection 224 is off the optical axis of the imaging lens 124. Therefore, neither the first reflection mirror 222 nor the second reflection mirror 224 is vertical to the optical path of the return light.

The first reflection mirror 222 and the second reflection mirror 224 have swing axes not parallel to each other, or preferably perpendicular to each other. Namely, the first reflection mirror 222 and the second reflection mirror 224 have a reflection face that enables one-dimensional scanning. The first reflection mirror 222 and the second reflection mirror 224; which have the reflection face that enables one-dimensional scanning, are referred to herein as one-dimensional scanning mirror or merely scanning mirror. The first one-dimensional scanning mirror 222 and the second one-dimensional scanning mirror 224 preferably scan a beam of light in a direction perpendicular to each other. Therefore, for example, the first scanning mirror 222 is swung about an axis parallel to the drawing, and the second scanning mirror 224 is swung about an axis perpendicular to the drawing.

The return light from the specific minute region of the subject 110 is reflected sequentially by the first scanning mirror 222 and the second scanning mirror 224 after the lights have passed through the converging optical system 104, and then strikes the end face of the light guide 142. The first scanning mirror 222 and the second scanning mirror 224 are swung about their respective axes, whereby the minute region on the subject 110 conjugate to the end face of the light guide 142 is scanned in a two-dimensional manner. Namely, the first one-dimensional scanning mirror 222 and the second one-dimensional mirror 224 scan the minute region on the subject 110 cooperatively in a two-dimensional manner.

Therefore, while the minute region is scanned in a two-dimensional manner by the first scanning mirror 222 and the second scanning mirror 224; the reflected or scattered light from the minute region on the subject 110 is scanned by the light detecting section 108. An image within the scanning range of the subject 110 is obtained by processing a scanning signal and a detecting signal all together.

In the light scanning optical device 100 according to this modification, since there is no obstacle on the optical path of the reflected or scattered light, the device has a high efficiency of light utilization. In addition, since the light strikes slantly the scanning mirrors 222 and 224, the optical device is advantageous in removing a stray light.

In the light scanning optical device 100 according to this modification, two-dimensional scanning is performed by employing two one-dimensional scanning mirrors 222 and 224. The light scanning optical device 100, however, may comprise one one-dimensional scanning mirror, and may be swung entirely in a one-dimensional manner by a piezoelectric element or the like in a direction different from the mirror, in order to perform two-dimensional scanning. Such arrangement is advantageous in simplification of an optical system and prevention of the lowered efficiency of light utilization due to a loss of mirror reflection.

Figure 12:
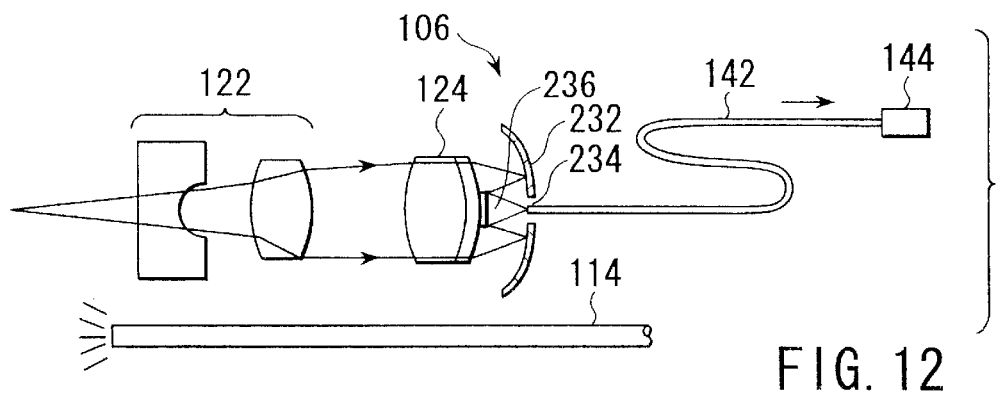
FIG. 12 schematically shows a light scanning optical device as a ninth modification of the light scanning optical device according to the first embodiment of the present invention.

In a ninth modification of the light scanning optical device according to the first embodiment, as shown in FIG. 12, the scanning section 106 comprises: a first reflection mirror 232 for returning an optical path of the return light from the imaging lens 124; and a second reflection mirror 236 for returning an optical path of the return light reflected by the first reflection mirror 232. The first reflection mirror 232 and the second reflection mirror 236 cross an optical axis of the imaging lens 124.

The first reflection mirror 232 has at its center an opening 234, which allows the return light to pass through, and is scanned in a two-dimensional manner. Here, this reflection mirror is referred to as a scanning mirror. The second reflection mirror 236 is fixed to the center of the imaging lens 124. Here, this reflection mirror is referred to as a fixed mirror.

Further, the scanning mirror 232 has a curved reflection face. The curved reflection face of the scanning mirror 232 has a function of lens, a function for removing aberration, etc. This is advantageous in reduction of the number of parts, or improvement of the degree of design freedom of an optical system.

The scanning mirror may have a function for changing the shape of the curved reflection face. That is, the scanning mirror 232 may be a variable converging scanning mirror. The variable converging scanning mirror changes the shape in accordance with an application of electric variable driving bias, and changes the focal point by changing the shape of the curved reflection face.

Figure 13:
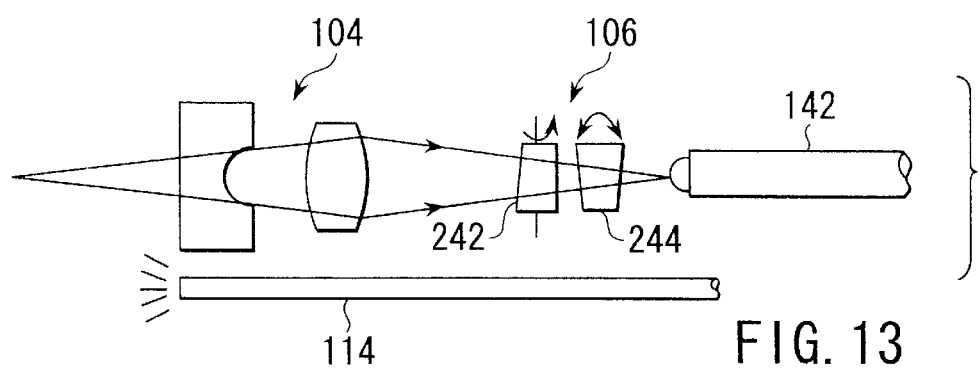
FIG. 13 schematically shows a light scanning optical device as a tenth modification of the light scanning optical device according to the first embodiment of the present invention.

In a tenth modification of the light scanning optical device according to the first embodiment, as shown in FIG. 13, the scanning section 106 comprises: a first prism 242 for refracting the light from the imaging lens 124; and a second prism 244 for refracting the lights that passes through the first prism 242.

The first prism 242 can be swung about a first axis, and the second prism 244 can be swung or vibrated about a second axis that is not parallel to the first axis. Therefore, the first prism 242 can refract the passing light in an arbitrary direction in a first plane, and the second prism 244 can refract the passing light in a direction in a second plane that is not parallel to the first plane.

Therefore, the minute region on the subject 110 conjugate to the end face of the light guide 142 is scanned in a one-dimensional manner in their corresponding directions by swinging or vibration of the first and second prisms 242 and 244. The first and second prisms 242 and 244, which enables one-dimensional scanning, are referred to herein as one-dimensional scanning prism or merely a scanning prism.

The first and second one-dimensional prisms 242 and 244 preferably scan light in a direction perpendicular to each other. Therefore, for example, the first scanning prism 242 is-swung about an axis parallel to the drawing, and the second scanning prism 244 is swung about an axis perpendicular to the drawing.

Figure 14:
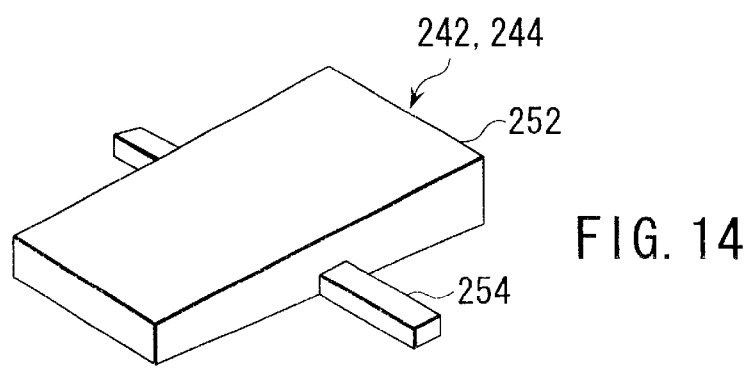
FIG. 14 is a partial perspective view of a prism shown in FIG. 13.

The first scanning prism has the same structure as the second scanning prism 244. Each of the scanning prisms 242 and 244 has a prism main body 252 and a pair of hinges 254 protruded from the side face of the pair, as shown in FIG. 14, and the hinges 254 are fixed to a fixing frame (not shown). Vibration is externally applied to the scanning prism 242 by a piezoelectric element or the like, whereby the prism main body 252 is swung or vibrated about an axis that passes through the hinge 254.

The prism main body 252 has a pair of optical surfaces not parallel to each other. Its inclined direction, i.e., a direction in which an inclination between these surfaces is the greatest is parallel to a plane perpendicular to the swing axis. Therefore, the prism main body 252 is swung or vibrated, whereby the passing light is refracted in a direction in a plane perpendicular to the swing axis.

In FIG. 13, the return light from the specific minute region of the subject 110 passes the first scanning prism 242 and the second scanning prism 244 after it has been passed through the converging optical system 104, and then strikes the end face of the light guide 142. The first scanning prism 242 and the second scanning prism 244 are swung or vibrated about their respective axes, whereby the minute region on the subject 110 conjugate to the end face of the light guide 142 is scanned in a two-dimensional manner.

Therefore, while the first scanning prism 242 and the second scanning prism 244 are swung or vibrated at the horizontal frequency and the vertical frequency of the display, thereby scanning the minute region in a two-dimensional manner, the reflected or scattered light from the minute region on the subject 110 is detected by the light detecting section 108. An image within the scanning region of the subject 110 is obtained by processing a scanning signal and a detecting signal all together.

In the light scanning optical device according to the present modification, constituent elements of the converging optical system 104 and the constituent elements of the scanning section 106 are linearly disposed with the scanning section 106 not containing a member that interrupts the return light. Thus, this optical device is advantageous in improvement of efficiency of light utilization and reduction of device in diameter.

A scanning prism may be a pair of glass plates disposed so that a mutual inclination angle is changed in a one-dimensional manner via liquid such as water. For example, a pair of glass plates are linked with each other by bellows, and a liquid such as water is filled in a space formed by these plates. Inclination of a pair of glass plates is changed in a one-dimensional manner, whereby the minute region on the subject 110 conjugate to the end face of the light guide 142 is scanned in a one-dimensional manner.

Figure 15:
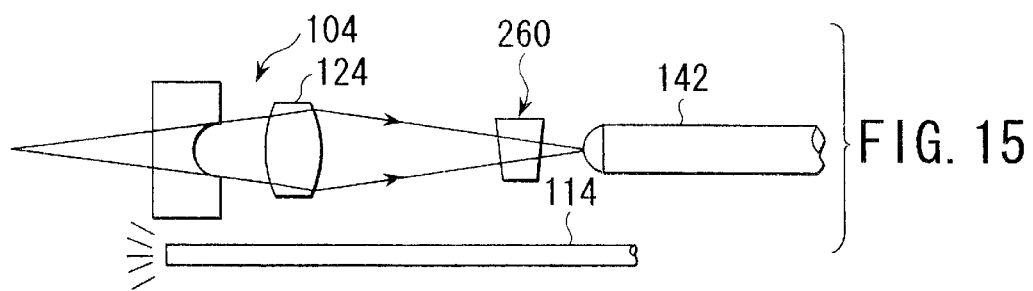
FIG. 15 schematically shows a light scanning optical device as an eleventh modification of the light scanning optical device according to the first embodiment of the present invention.

In an eleventh modification of the light scanning optical device according to the first embodiment, as shown in FIG. 15, the scanning section 106 comprises a prism 260 for refracting the light from the imaging lens 124. The prism 260 can be swung or vibrated about a first axis and about a second axis that is not parallel to the first axis. Therefore, the prism 260 can refract the passing light in an arbitrary direction.

Therefore, the minute region on the subject 110 conjugate to the end face of the light guide 142 is scanned in a two-dimensional manner by swinging or vibrating the prism 260 about the two axes. As understood from the above description, the prism 260 permits two-dimensional scanning. Here, this prism is referred to as a two-dimensional scanning prism or merely a scanning prism.

The two-dimensional scanning prism 260 preferably scans light in a direction perpendicular to another. Therefore, for example, the scanning prism 260 is swung or vibrated about an axis parallel to the drawing and about an axis perpendicular to the drawing.

Figure 16:
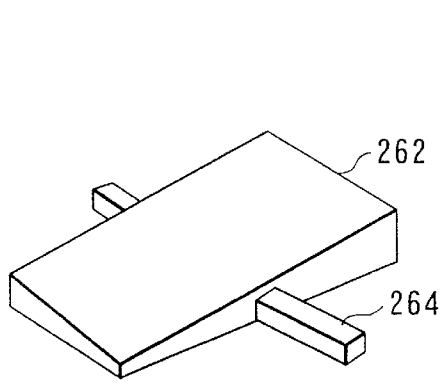
FIG. 16 is a partial perspective view of the prism shown in FIG. 15.
Figure 17:
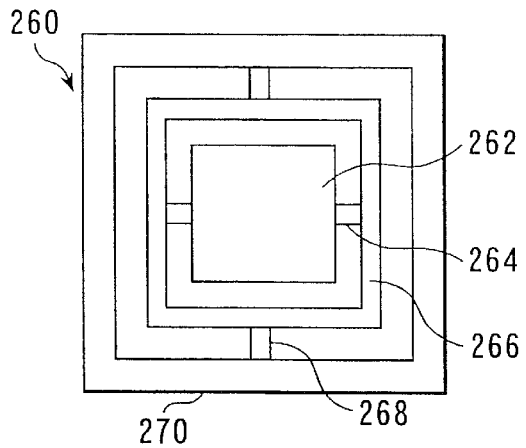
FIG. 17 is a plan view of the prism shown in FIG. 15.

The scanning prism 260 has a prism main body 262 and a pair of first hinges 264 protruded from the side face of the pair, as shown in FIG. 16. The hinge 264 is linked with a movable frame 266, as shown in FIG. 17. The movable frame 266 is linked with a fixing frame 270 via a second pair of hinges 268 extending in a direction perpendicular to the first pair of hinges 264. Vibration is externally applied by a piezoelectric element or the like, whereby the prism main body 262 is swung or vibrated about an axis that passes through the inside of the hinge 264 and about an axis that passes through the inside of the hinge 268.

The prism main body 262 has a pair of optical surfaces not parallel each other. Its inclined direction, i.e., a direction in which an inclination between these surfaces is greatest is not parallel to both of a plane perpendicular to a swing axis that passes through the inside of the hinge 264 and a plane perpendicular to a vibrating axis that passes through the inside of the hinge 268. Therefore, the swinging or vibration about the vibration axis that passes through the inside of the hinge 264 of the prism main body 262 refracts the light that passes through the hinge in a direction in a plane perpendicular to the periphery of the swing axis that passes through the inside of the hinge 264. In addition, the swinging or vibration about the vibration axis that passes through the inside of the hinge 268 of the prism main body 262 refracts the light that passes through the hinge in a direction in a plane perpendicular to the periphery of the swing axis that passes through the inside of the hinge 268.

In FIG. 15, the return light from the specific minute region of the subject 110 passes through the scanning prism 260 after it has passed through the light connecting optical system 104, and then strikes the end face of the light guide 142. The scanning prism 260 is swung or vibrated about two axes, whereby the minute region on the subject 110 conjugate to the end face of the light guide 142 is scanned in a two-dimensional manner.

Therefore, the scanning prism 260 is swung or vibrated at the horizontal frequency and vertical frequency of the display about their respective swing axes, whereby the minute region is scanned in a two-dimensional manner, while the reflected or scattered light from the minute region on the subject 110 is detected by the light detecting section 108, and a scanning signal and a detecting signal are processed all together, whereby an image within the scanning range of the subject 110 is obtained.

In the light scanning optical device according to this modification, constituent elements of the converging optical system 104 and constituent elements of the scanning section 106 are linearly scanned without the scanning section 106 containing a member that interrupts the return light. Thus, this optical device is advantageous in improvement of efficiency of light utilization and reduction of the device in diameter.

The scanning prism may be a pair of glass plates disposed so that a mutual inclination angle is changed in a two-dimensional manner via liquid such as water. For example, a pair of glass plates are linked with each other by bellows, and liquid such as water is filled in a space formed by these plates. An inclination of a pair of glass plates is changed in a two-dimensional manner, whereby the minute region on the subject 110 conjugate to the end face of the light guide 142 is scanned in a two-dimensional manner.

Figure 18:
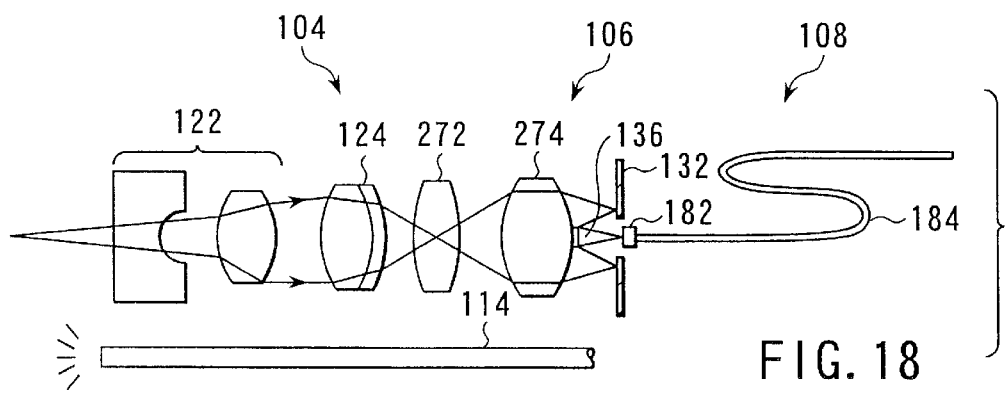
FIG. 18 schematically shows a light scanning optical device as a twelfth modification of the light scanning optical device according to the first embodiment of the present invention.

In a twelfth modification of the light scanning optical device according to the first embodiment, as shown in FIG. 18, there is provided a light guide 114 connected to a light source section 112. The converging optical system 104 comprises: an objective lens 122 facing the subject 110; an imaging lens 124 for imaging the light from the subject 110 that passes through the objective lens 122; a field lens 272 disposed on the image plane of the imaging lens 124; and a relay lens 274 for relaying an image on the image plane of the imaging lens 124. The scanning section 106 has a two-dimensional scanning mirror 132 and a fixed mirror 136. The fixed mirror 136 is provided at the center of the relay lens 274. The light detecting section 108 comprises a light detector 182 disposed on the image plane of the relay lens 274.

The relay lens 274 expands the scanning region of the minute region conjugate to the light receiving face of the light detector 182 caused by the scanning mirror 132. Therefore, in the light scanning optical device according to this modification, an image of the subject 110 can be produced at a sufficiently wide imaging angle.

Figure 19:
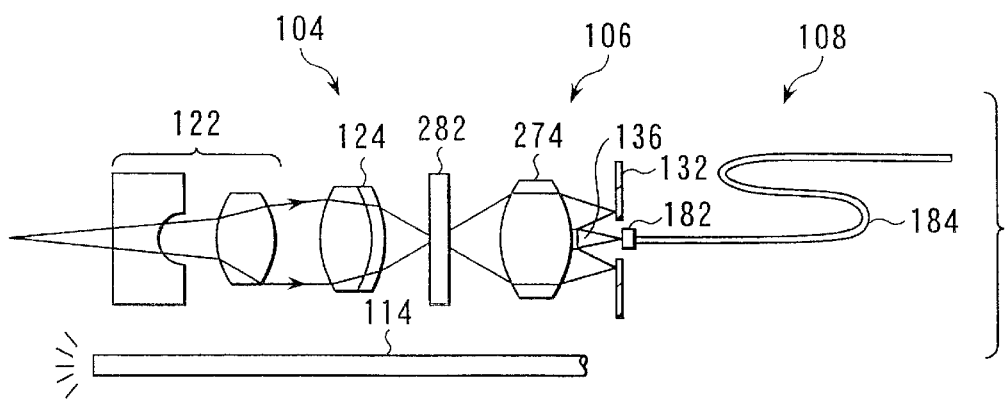
FIG. 19 schematically shows a light scanning optical device as a thirteenth modification of the light scanning optical device according to the first embodiment of the present invention.

In a thirteenth modification of the light scanning optical device according to the first embodiment, as shown in FIG. 19, there is provided a light guide 114 connected to the light source section 112. The converging optical system 104 comprises: an objective lens 122 facing the subject 110; an imaging lens 124 for imaging the light from the subject 110 that passes through the objective lens 122; an optical function plate 282 disposed on the image plane of the imaging lens 124; and a relay lens 274 for relaying an image on the image plane of the imaging lens 124. The scanning section 106 has a two-dimensional scanning mirror 132 and a fixed mirror 136. The fixed mirror 136 is provided at the center of the relay lens 274. The light detecting section 108 comprises a light detector 182 disposed on the image plane of the relay lens 274.

The optical function plate 282 is a functional plate that has a light accumulating function such as fluorescent plate or imaging plate or the like, for example. The optical function plate 282 may be another functional plate that has a light accumulating function. In addition, the optical function plate 282 may be a light amplifier element having EL (electroluminescence) structure applied thereto, a light amplifier element formed of a compound semiconductor, or a microchannel plate.

The light scanning optical device according to the present modification includes a functional plate that has a light accumulating function on the image plane of the imaging lens 124, and thus has high light sensitivity. This optical device is advantageous in insufficient light quantity of the return light from the subject.

Figure 20:
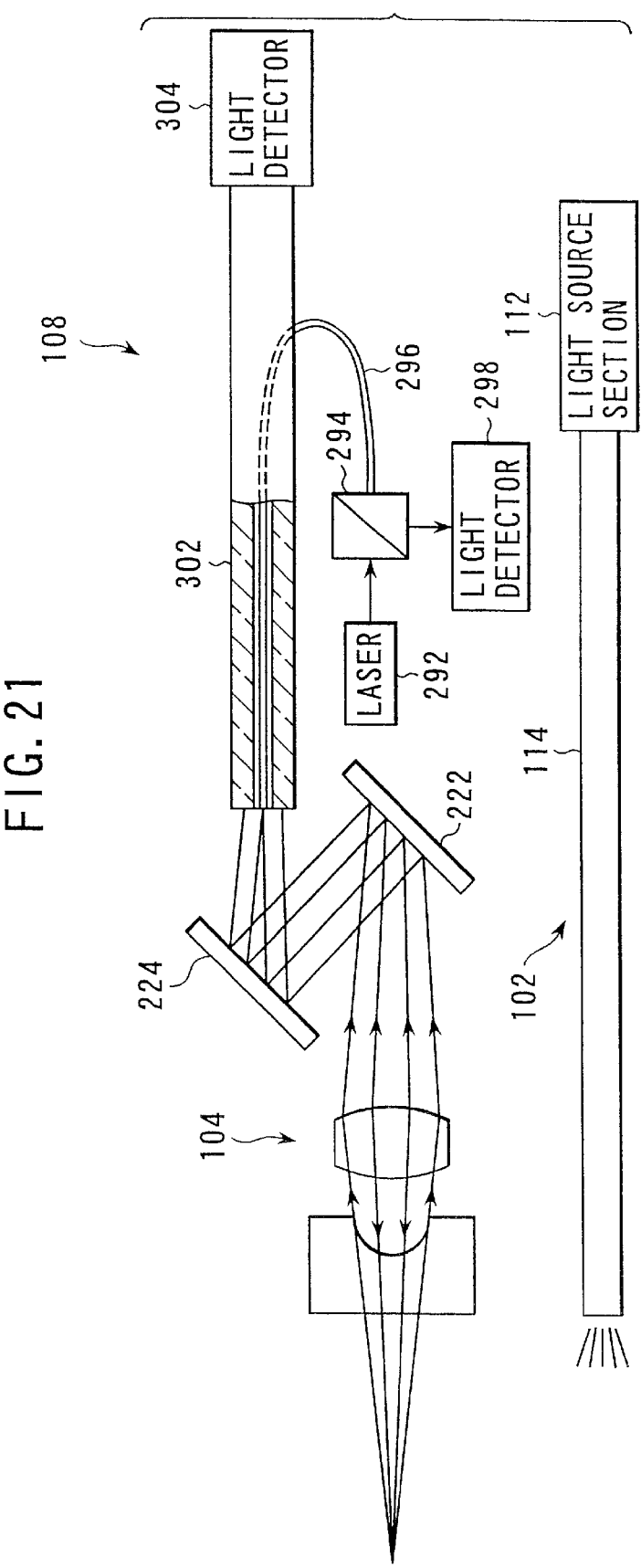
FIG. 20 schematically shows a light scanning optical device as a fourteenth modification of the light scanning optical device according to the first embodiment of the present invention.

In a fourteenth modification of the light scanning optical device according to this modification, as shown in FIG. 20, the light detecting section 108 comprises: a light guide 302 having an end face disposed on the image plane of the converging optical system 104; a light detector 304 for converting the return light received from the light guide 302 into an electrical signal; and a confocal optical system for producing a confocal image.

Figure 21:
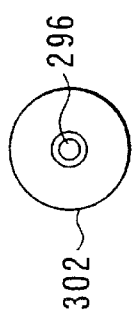
FIG. 21 shows an end face of an optical fiber and a light guide that are coaxially disposed as shown in FIG. 20.

The confocal optical system comprises: an illumination laser 292; a beam splitter 294 for separating the forward light and the return light; an optical fiber for guiding the forward light and the return light; and a light detector 298 for detecting the return light. The optical fiber is coaxially embedded in the light guide 302, as shown in FIG. 21, intermediately of the light guide 302.

The optical fiber has an end face disposed on the image plane of the converging optical system 104, and this end face functions as a pin hole. The optical fiber is a single mode optical fiber, for example. The optical fiber may be a single mode optical fiber amplifier to improve the light sensitivity of a co-formal optical image.

The laser light emitted from the illumination laser 292 passes through the beam splitter 294, propagates the inside of the optical fiber 296, and is projected from the end face disposed on the image plane of the light connecting optical system 104. Then, the laser light is focused at a point by the converging optical system 104 via two one-dimensional scanning mirrors 224 and 222. The return light from a point of the subject positioned at the focused point returns back along the optical path of the forward light. Then, the return light enters the optical fiber 296 from its end face, and propagates its inside. Then, the light is directed to the light detector 298 by the beam splitter 294, and is subject to photoelectrical conversion by the light detector 298.

The end face of the optical fiber 296 functions as a pin hole. Thus, light from points off a point conjugate to the end face of the optical fiber 296 does not reach the end face of the optical fiber 296. Therefore, while laser light is scanned by two scanning mirrors 222 and 224, the return light is detected by the light detector 298, and a scanning signal and a detecting signal are processed all together, whereby a confocal image within the scanning range of the subject 110 is obtained.

In addition, the light illuminated by the illumination unit 102 and reflected or scattered in the minute region at a position conjugate to the end face of the light guide 302 advances to the inside of the light guide 302 through the converging optical system 104 and the two scanning mirrors 222 and 224. Then, the light propagates its inside, and is subject to photoelectrical conversion by the light detector 304. The detecting signal and the scanning signal are processed by the light detector 304 all together, whereby a normal image within the scanning range of the subject 110 is obtained In the light scanning optical device according to this modification, the light detecting section 108 comprises a confocal optical system. Thus, a confocal image as well as normal image within the scanning range of the subject 110 is obtained.

Figure 22:
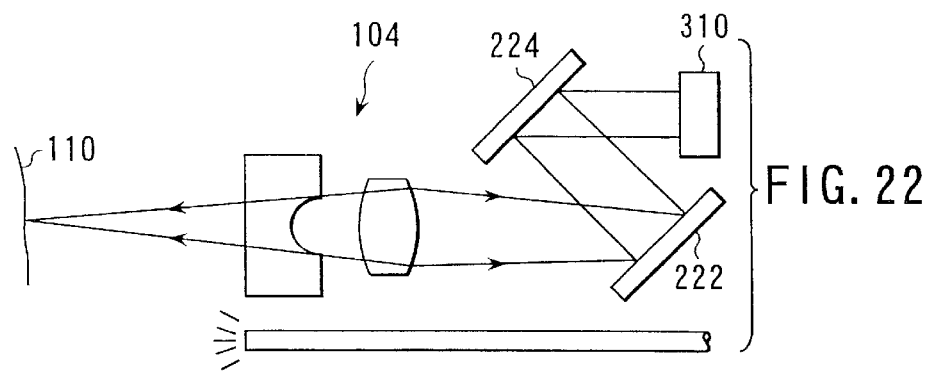
FIG. 22 schematically shows a light scanning optical device as a fifteenth modification of the light scanning optical device according to the first embodiment of the present invention.
Figure 23:
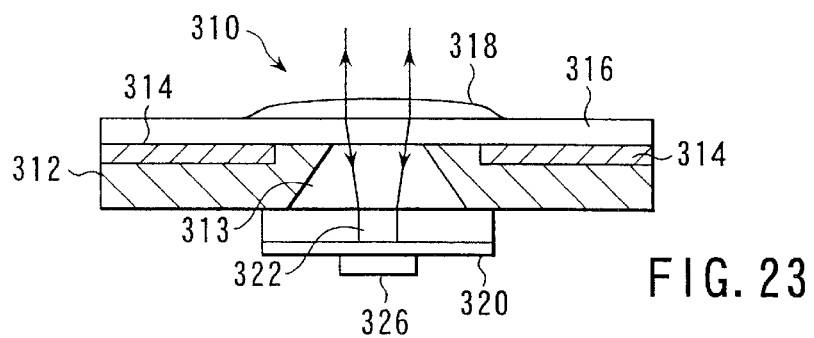
FIG. 23 shows a section of an integrated light receiver shown in FIG. 22.

In a fifteenth modification of the light scanning optical device according to the first embodiment, as shown in FIG. 22, the light detecting section 108 comprises an accumulation type light receiver 310. The accumulation type light receiver 310 comprises: a through hole 313; a substrate 312 having a first ring shaped light receiving element 314 formed at the periphery of the hole: an optically transparent SiO₂ film 316, which covers the through hole 313 and the first light receiving element 314; a converging lens 318 formed on the film; a light emitting element 320 having a light emitting region 322, which has a minute light emitting face; and a second light receiving element 326 for detecting the light that passes through the light emitting region 322 of the light emitting element 320.

The laser light emitted from the light emitting element 320 passes through the through hole 313 of the substrate 312, the SiO₂ film 316, and the converging lens 318, and is projected out of the accumulation type light receiver 310. The laser light projected from the accumulation type light receiver 310 is focused at a point by the converging optical system 104 via two one-dimensional scanning mirrors 224 and 222. The return light from a point of the subject positioned at the focused point returns back along an optical path of the forward light, passes through the light emitting region 322 of the light emitting element 320, and is subject to photoelectrical conversion by the second light receiving element 326.

The light emitting region 322 of the light emitting element 320 has the minute light emitting face. Thus, the light from points off a point conjugate to the light emitting face of the light emitting element 320 does not arrive at the light emitting region 322 of the light emitting element 320. Therefore, while laser light is scanned by two scanning mirrors 222 and 224, the return light to the second light emitting element 26 is detected, and a scanning signal and a detecting signal are processed all together, whereby a confocal image within the scanning range of the subject 110 is obtained.

In addition, the reflected or scattered light from a region, which is illuminated with the light guide 114 connected to the light source 112 and is conjugate with respect to the first light receiving element 314, arrives at the first light receiving element 314 through the converging optical system 104 and the two scanning mirrors 222 and 224, and is subject to photoelectrical conversion. The detecting signal caused by the first light receiving element 314 is processed together with a scanning signal, whereby a normal image within the scanning range of the subject 110 is produced.

In the light scanning optical device according to this modification, since the light detecting section 108 includes a confocal optical system, the light scanning optical device can acquire a confocal image in addition to a normal image within the scanning range of the subject 110.

Figure 24:
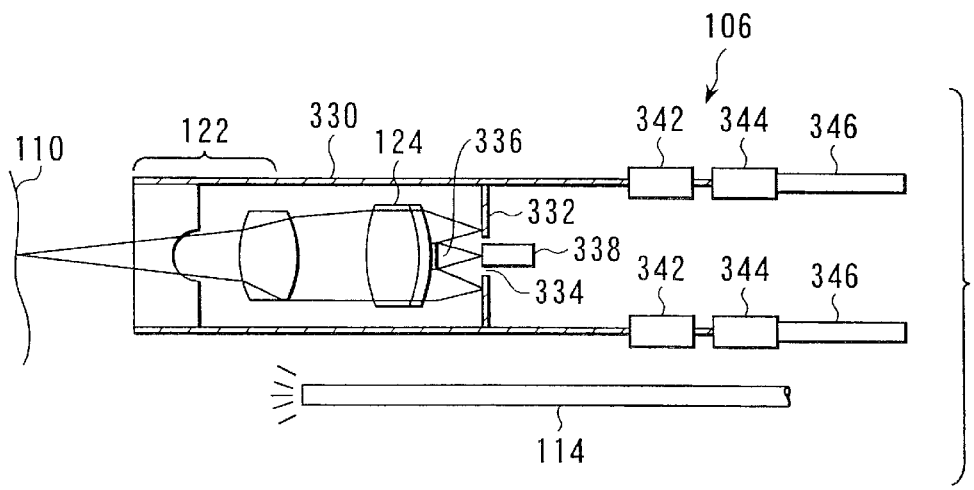
FIG. 24 schematically shows a light scanning optical device as a sixteenth modification of the light scanning optical device according to the first embodiment of the present invention.

In a sixteenth modification of the light scanning optical device according to the first embodiment, as shown in FIG. 24, there is provided the light guide 114 connected to the light source 112. The converging optical system 104 comprises: an objective lens 122 facing the subject 110; an imaging lens 124 for imaging the return light that passes through the objective lens 122; a first reflection mirror 332 for returning an optical path of the return light from the imaging lens 124; and a second reflection mirror 336 for returning an optical path of the return light reflected by the first reflection mirror 332 again. These optical elements are linearly arranged and fixed in one unit 330 together.

The first reflection mirror 332 has an opening 334 at its center, and the light detecting section 108 comprises a light detector 338 mounted to the opening 334 of the first reflection mirror 332.

The scanning section 106 comprises: a first one-dimensional drive piezoelectric vibrator 342 for scanning a unit 330 in a first direction; and a second one-dimensional drive piezoelectric vibrator 334 for scanning the unit 330 in a second direction. These piezoelectric vibrators 342 and 344 are supported by a fixed support section 346.

For example, the first piezoelectric vibrator 342 swings the unit 330 in a direction parallel to the drawing, and the second piezoelectric vibrator 344 swings in a direction perpendicular to the drawing. As understood from the above description, the unit 330 is swung in a two-dimensional manner, and the minute region on the subject 110 conjugate to the light receiving face of the light detector 338 is scanned in a two-dimensional manner.

Therefore, while the unit 330 is swung in a two-dimensional manner at the horizontal frequency and vertical frequency of the display, such that the minute region conjugate to the light receiving face of the light detector 338 is scanned in a two-dimensional manner, the reflected or scattered light from the subject 110 that exists in the minute region is detected by the light detector 338, and a scanning signal and a detecting signal are processed all together, whereby an image within the scanning range of the subject 110 is obtained.

In the light scanning optical device according to this modification, constituent elements of the converging optical system is linearly arranged, and thus, is advantageous in reducing the device in diameter. The first reflection mirror 332 and the second reflection mirror 336 may be omitted. Although the light scanning optical device in which the first reflection mirror 332 and the second reflection mirror 336 are omitted requires a long inflexible portion relevant to application to the endoscope, the device is advantageous in improvement of lowered efficiency of light utilization caused by reflection. In the light scanning optical device according to this modification, although all constituent elements of the converging optical system is swung, only the objective lens 122 is swung.

Figure 25:
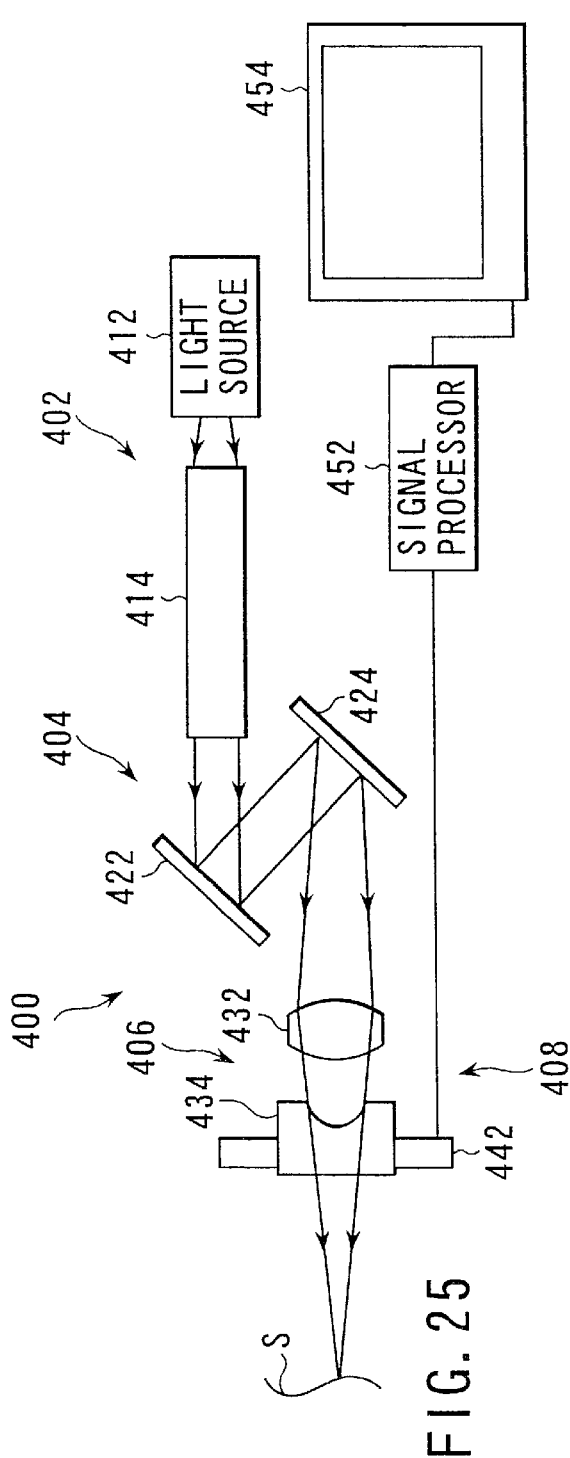
FIG. 25 schematically shows a light scanning optical device according to a second embodiment of the present invention.

As shown in FIG. 25, the light scanning optical device 400 according to a second embodiment of the present invention comprises: a light source section 402 for projecting a light beam; a scanning section 404 for scanning the light beam; a converging optical system 406 for converging the light beam; and a detecting section 408 for detecting the return light from the subject S.

The light source section 402 comprises a light source 412 for emitting light; a light guide 414, which takes into the light from the light source 412 at one end and projects the light beam from the other end. The light source 412 sequentially emits the colored lights of RGB, for example.

The scanning section 404 comprises: a first one-dimensional scanning mirror 422 and a second one-dimensional scanning mirror 424. The first one-dimensional scanning mirror 422 directs the light beam projected from the light guide 414 to the second one-dimensional scanning mirror 424; and the second one-dimensional scanning mirror 424 directs the light beam from the first one-dimensional scanning mirror 422 to the converging optical system 406.

The first one-dimensional scanning mirror 422 and second one-dimensional scanning mirror 424, which have a reflecting surface, respectively, are swingable about axes non parallel to each other. For example, the first one-dimensional scanning mirror 422 has a reflection face, which can swing about an axis parallel to the drawing, and the second one-dimensional scanning mirror 424 has a reflection face, which can swing about an axis vertical to the drawing.

A preferable one-dimensional scanning mirror is a micro-machine mirror produced by employing a semiconductor manufacturing process, for example. This semiconductor manufacturing process enables to process in order of $\mu$m, and the thus produced micro-machine mirror is very small. This contributes to device miniaturization. The micro-machine manufacturing process is managed under a very generous rule compared with a charge coupled device, and thus the micro-machine mirror can be manufactured more inexpensively than the charge coupled device. Although such one-dimensional scanning mirror is driven by an electrostatic system, for example, the mirror may be driven by an electromagnetic system or a piezoelectric system.

The converging optical system 406 comprises a lens system having a lens 432 and a lens 434. This lens system converts a divergent light beam from the scanning mirror 424 to a convergent light beam.

The light detecting section 408 comprises a ring-shaped photodiode 442 surrounding the lens 434. The ring-shaped photodiode 442 receives the reflected or scattered light from the subject S, and converts the light into an electric signal according to its intensity. The light detecting section 408 may comprise a non-ring-shaped photodiode, an Avalanche photodiode, a pin photodiode, or a photomultiplier instead of the ring-shaped photodiode 442.

In FIG. 25, the light emitted from the light source 412, for example, the sequentially emitted colored light of RGB enters the light guide 414 at one end, propagates its inside, and is projected from the other end. The light beam projected from the light guide 414 is reflected by the first scanning mirror 422 and the second scanning mirror 424, and then, is converted into a convergent light beam by a lens system having the lens 432 and the lens 434.

The convergent light beam striking the subject forms a light spot at its surface or inside at which the light is reflected or scattered. A part of the light reflected or scattered from the subject S is subject to photoelectrical conversion by the ring-shaped photodiode 442.

The first scanning mirror 422 and the second scanning mirror 424 each swing a reflection face, for example, about axes perpendicular to each other, and the light beam is scanned in a two-dimensional manner accordingly. As a result, the return light from the subject S, i.e., the light spot, which is a source of the reflected light or scattered light, is also scanned in a two-dimensional manner, for example, raster-scanned. Namely, the first scanning mirror 422 and the second scanning mirror 424 scan the light spot on the subject S in a two-dimensional manner in cooperation with each other.

An output signal of the ring-shaped photodiode 422, which is inputted to a signal processor 452, is processed together with a scanning signal of a scanning mirror, whereby an image within the scanning region of the subject S is obtained. This processing is performed for each of the colored lights of RGB, and the image of each color is composed, whereby a color image within the scanning region of the subject S is obtained. The produced image is displayed on a monitor 454, for example.

The resolution of the thus produced image depends on the size of the light spot formed by the converging optical system 406 converging the light beam. The converging optical system 406 can narrow the light spot to the size of 1 $\mu$m or less in diameter. Therefore, this light scanning optical device can achieve the resolution of 1 $\mu$m. Thus resolution is much higher than the resolution of the charge coupled device.

In observing the subject S, true-zoom like observation may be performed. That is, at the beginning of observation, the scanning region is set to be relatively large, whereby the entire image of the observation region of the subject is grasped. Then, by narrowing the scanning region, a part to be particularly observed in detail may be observed at high sensitivity and high speed.

As understood from the above description, the light scanning optical device according to the second embodiment can produce an image of the subject with high resolution without employing a charge coupled device such as relatively expensive CCD.

The light scanning optical device according to the present invention is not limited to the aforementioned second embodiment, and various modifications or changes can be made without departing the scope of the invention.

Figure 26:
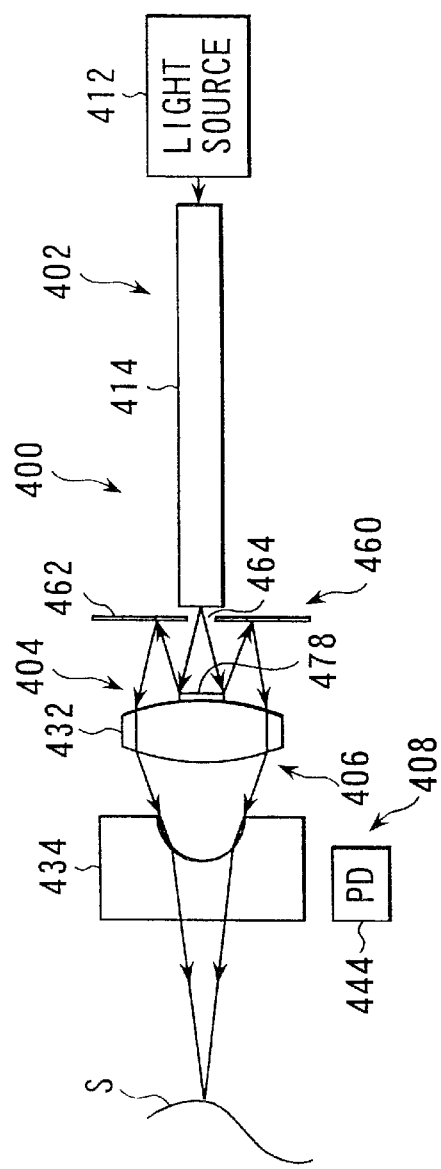
FIG. 26 schematically shows a light scanning optical device as a first modification of the light scanning optical device according to the second embodiment of the present invention.

In the first modification of the light scanning optical device according to the second embodiment, as shown in FIG. 26, the light detecting section 408 comprises a photodiode 444 disposed near the lens 434. The scanning section 404 comprises: a two-dimensional scanning mirror 460 having at its center an opening 464, which allows the light beam projected from the light guide 414 to pass through; and a fixed mirror 478 for returning the light beam that passes through the opening 464 of the two-dimensional scanning mirror 460 toward the two-dimensional scanning mirror 460. The two-dimensional scanning mirror 460, which comprises a reflection face swingable about two axes perpendicular to each other, reflects the light beam from the fixed mirror 478 toward the lens 432.

The fixed mirror 478, which is supported by the lens 432, is positioned at the center of lens 432. The fixed mirror 478 is produced by selectively vapor-depositing metal on the optical surface of the lens 432, for example.

Figure 27:
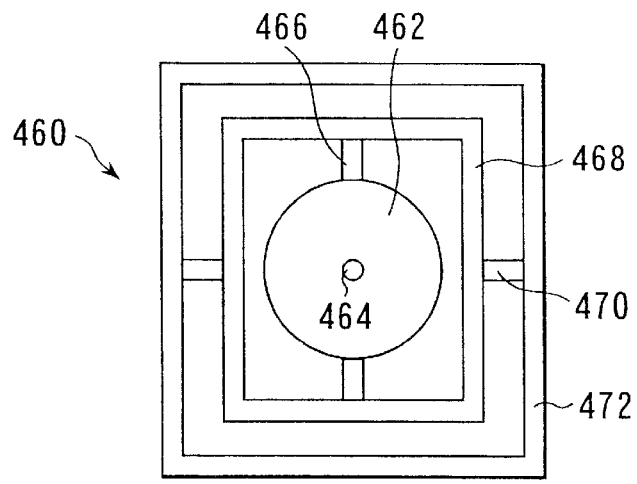
FIG. 27 schematically shows a two-dimensional scanning mirror shown in FIG. 26.

The two-dimensional scanning mirror 469, for example, as shown in FIG. 27, has a so-called gimbal structure. The scanning mirror comprises: a reflection face 462 having an opening 464 at its center; a first pair of hinges 466 extending from the reflection face 462 to both sides along a first axis; a movable frame 468 for supporting the reflection face 462 via the first pair of hinges 466; a second pair of hinges 470 extending from the movable frame 468 to both ends along a second axis perpendicular to the first axis; and a fixed frame 472 for supporting the movable frame 468 via the second pair of hinges 470.

A preferable two-dimensional scanning mirror is a micro-machine mirror produced by employing a semiconductor manufacturing process as in the aforementioned one-dimensional scanning mirror. This micro-machine mirror can be manufactured very small and more inexpensively than the charge coupled device. The two-dimensional scanning mirror is driven by an electrostatic system, an electromagnetic system, or a piezoelectric system, for example, such that the reflection face 462 is swung about a first axis, and swung about the second axis together with the movable frame 468. Namely, the reflection face 462 is swung about two axes perpendicular to each other.

The mixed mirror 478 and the two-dimensional scanning mirror 460 cross the optical axis of the converging optical system 406 all together. Therefore, the lens 434, lens 432, fixed mirror 478, and scanning mirror 460 are linearly arranged each other. Such layout is advantageous in reducing the light scanning optical device 400 in a diameter and reducing the scanning section 404 and the converging optical system 406 in full length.

Figure 28:
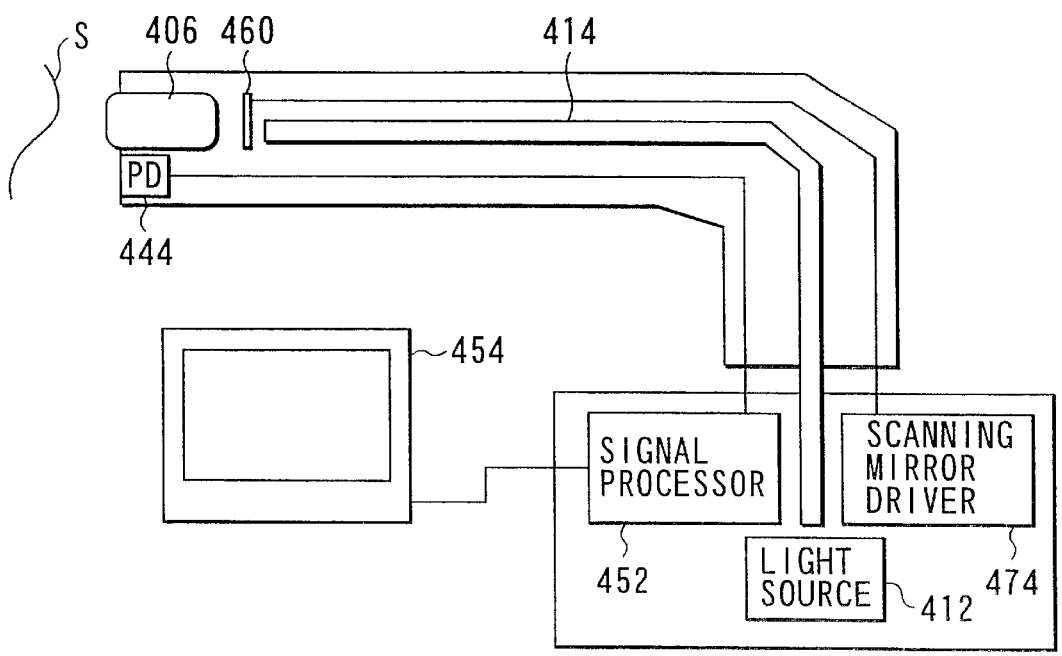
FIG. 28 schematically shows an endoscope having the light scanning optical device shown in FIG. 26 incorporated therein.

An endoscope having such light scanning optical device incorporated therein is shown in FIG. 28. In FIG. 28, the light source 412 sequentially emits the colored lights of RGB. The colored lights of RGB enter the light guide 414 at one end, propagates its inside, and is projected from the other end. The light beam projected from the light guide 414 is projected to the outside of the endoscope through the two-dimensional scanning mirror 460 and the converging optical system 406. The two-dimensional scanning mirror 460 is driven by the scanning mirror driver 474. The light beam projected from the endoscope is scanned in a two-dimensional manner in accordance with the driving of the two-dimensional scanning mirror 460.

A part of the lights reflected or scattered at the subject S is subject to photoelectrical conversion by the photodiode 444. An output signal of the photodiode 444, which is inputted in the signal processor 452, is processed together with the scanning signal from the scanning mirror driver 474, whereby the image of each color of RGB within the scanning range of the subject S is obtained. The image of each color of RGB is composed, whereby the color image within the scanning range of the subject S is obtained. The produced color image is displayed on the monitor 454, for example.

In this endoscope, the viewing direction of the light scanning optical device coincides with the insert direction of the endoscope. Therefore, the endoscope is a so-called straightforward viewing type endoscope in which the insert direction and viewing direction coincide with each other, which is very preferable in operability. The light scanning optical device 400 is reduced in diameter by using a scanning mirror of a micro-machine mirror, and is preferably incorporated into the distal end of the endoscope. In addition, the full length of the scanning section 404 is reduced, and thus, the endoscope has a short inflexible portion.

Figure 29:
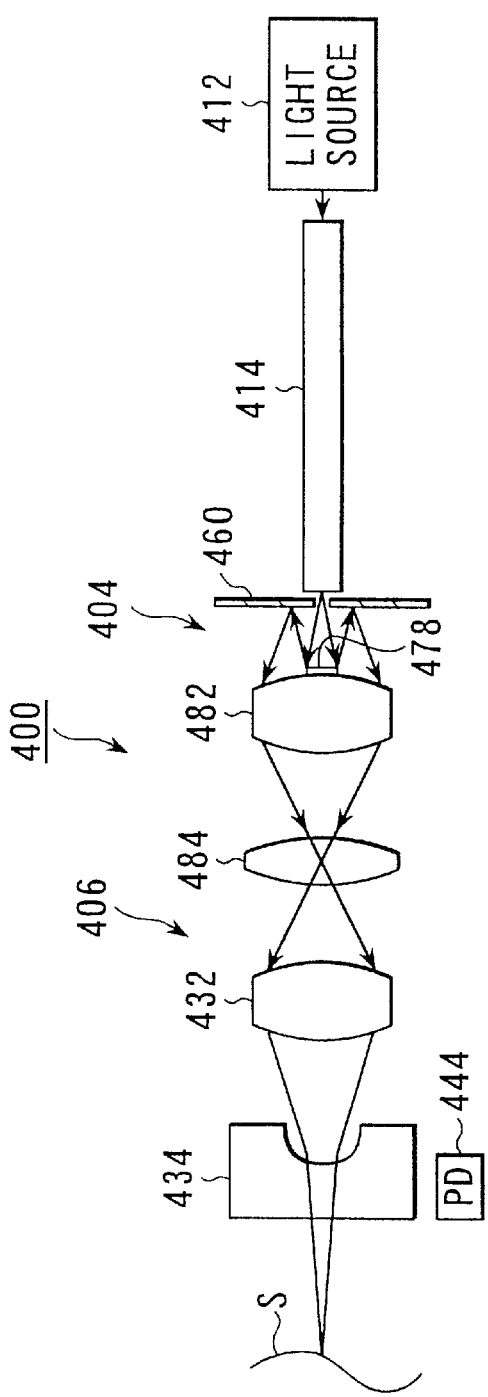
FIG. 29 schematically shows a light scanning optical device as a second modification of the light scanning optical device according to the second embodiment of the present invention.

In the second modification of the light scanning optical device according to the second embodiment, as shown in FIG. 29, the converging optical system 406 comprises: a lens system consisting of the lens 432 and the lens 434; an imaging lens 482 for converting the divergent light beam projected from the end face of the light guide 414 into the convergent light beam, and in other word, for imaging an image on the end face of the light guide 414; and a field lens 484 disposed on the image plane of the imaging lens 482. The scanning section 404 has a two-dimensional scanning mirror 460 and a fixed mirror 478, and the fixed mirror 478 is provided at the center of the imaging lens 482.

The lens system having the lens 432 and the lens 434 functions as a relay lens system, and expands and transmits movement of a converging point on the image plane of the imaging lens 482 caused by the scanning mirror 460. In addition, an image is relayed optically and preferably by the field lens 484. Therefore, the light scanning optical device according to this modification can acquire an image of the subject S at a sufficiently wide imaging angle.

Figure 30:
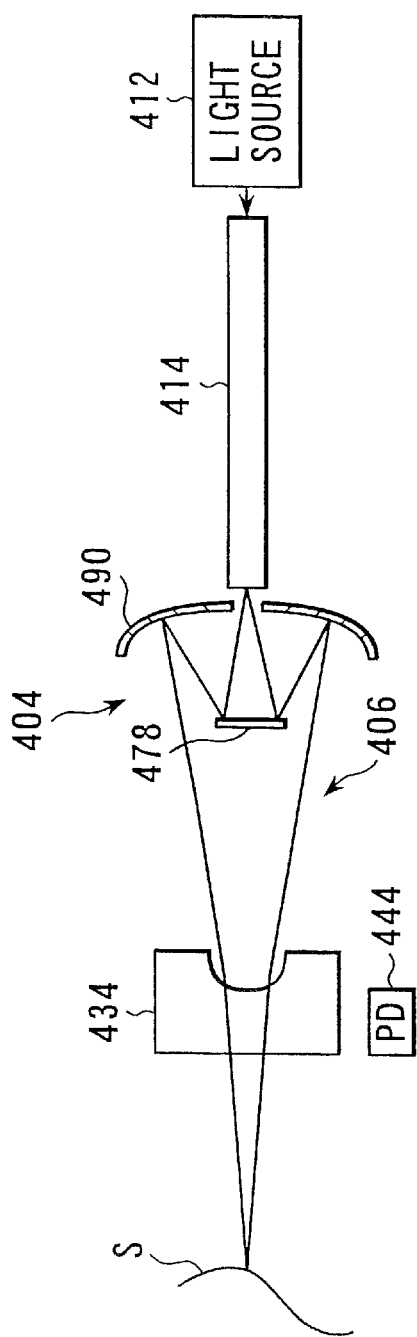
FIG. 30 schematically shows a light scanning optical device as a third modification of the light scanning optical device according to the second embodiment of the present invention.

In the third modification of the light scanning optical device according to the second embodiment, as shown in FIG. 30, the scanning section 404 comprises a fixed mirror 478 and a variable converging two-dimensional scanning mirror 490 having a converging function. The converging optical system 406 comprises the lens 434 and the variable converging two-dimensional scanning mirror 490. Namely, the variable converging two-dimensional scanning mirror 490 is commonly included in the scanning section 404 and the converging optical system 406.

The variable converging two-dimensional scanning mirror 490 has a reflection face swingable about two axes perpendicular to each other. In this regard, this scanning mirror is similar to the aforementioned two-dimensional scanning mirror 460. The variable converging two-dimensional scanning mirror 490 has the reflection face, which has positive power, and therefore, has a converging function. Further, the variable converging two-dimensional scanning mirror 490, which has a function for changing the curved shape of the reflection face, can change a focal point of the reflection face. This makes it possible to move an observation face in an optical axis direction without moving the light scanning optical device.

Figure 31:
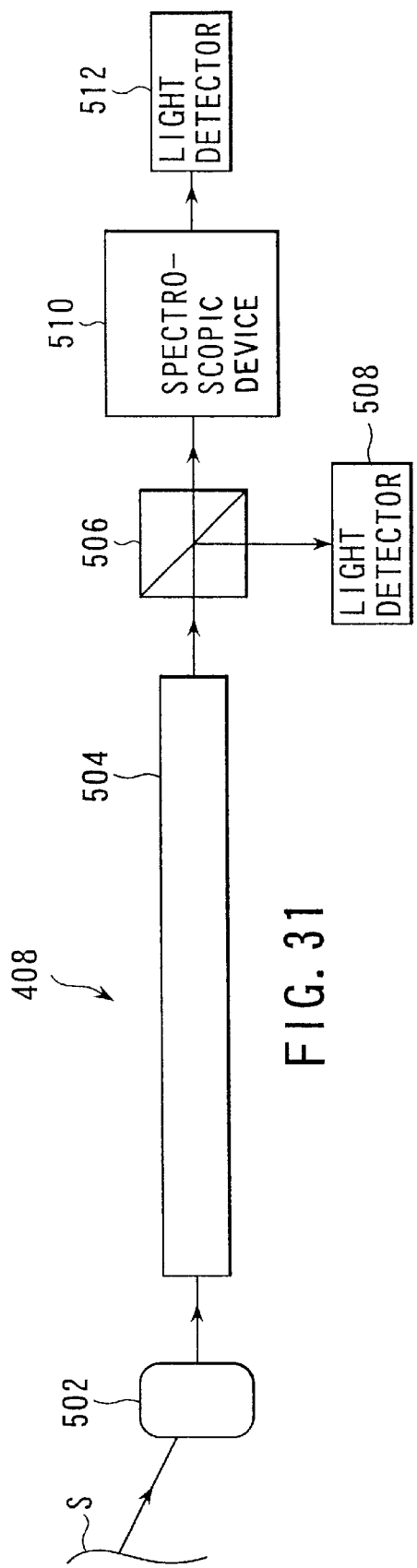
FIG. 31 schematically shows a light detecting section of a light scanning optical device as a fourth modification of the light scanning optical device according to the second embodiment of the present invention.

In the fourth modification of the light scanning optical device according to the second embodiment, as shown in FIG. 31, the light detecting section 408 comprises: an objective lens 502 for picking up the return light from the subject S; a light guide 504 for guiding the light focused by the objective lens 502; a beam splitter 506 for splitting into two light beams projected from the light guide 504; a light detector 508 for detecting one divided light beam; a spectroscopic device 510 for spectroscopically dispersing the other divided light beam; and a light detector 512 for detecting the spectroscopically dispersed light. The spectroscopic device 510 is a spectroscope, for example, and may be a diffraction lattice or a prism.

The return light from the subject S enters the light guide 504 through the objective lens 502. The light beam projected from the light guide 504 is divided into two beams by the beam splitter 506. One beam directly reaches the light detector 508, and is thus subject to photoelectrical conversion. The other beam reaches the light detector 512 through the spectroscopic device 510, and is thus subject to photoelectrical conversion.

According to the light scanning optical device according to this modification, light of a desired wavelength is selected by a spectroscopic device 510, whereby fluorescence specified to the lesion is detected, and its fluorescent image is obtained. Namely, the light scanning optical device according to this modification can perform fluorescence observation as well as general observation. The lesion may generate specific fluorescence, thus making it possible to diagnose the lesion based on such fluorescence observation.

Figure 32:
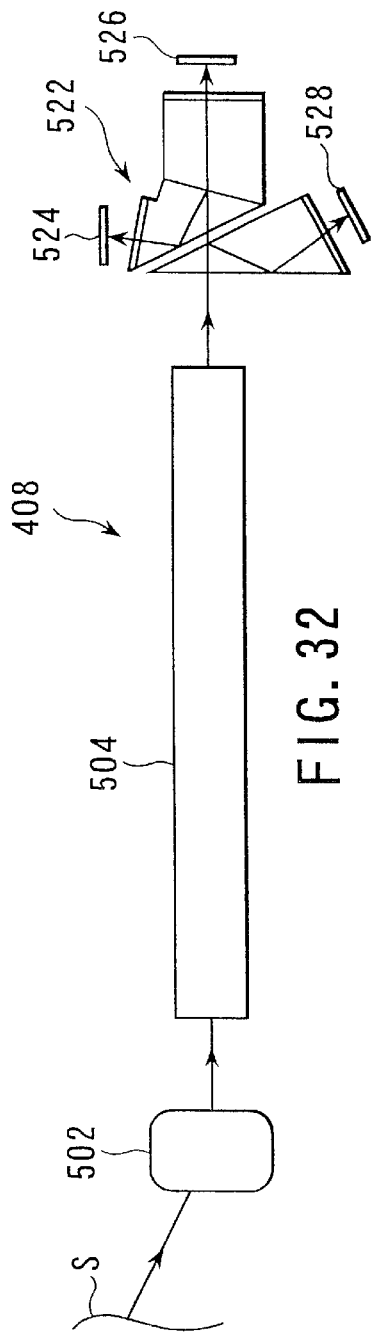
FIG. 32 schematically shows a light detecting section in a light scanning optical device as a fifth modification of the light scanning optical device according to the second embodiment of the present invention.

In a fifth modification of the light scanning optical device according to the second embodiment, the light source 412 of the light source section 402 emits white color light. The light detecting section 408 comprises: an objective lens for picking up the return light from the subject S; a light guide 504 for guiding the light focused by the objective lens 502; a color decomposing prism 522 for dividing the light beam projected from the light guide 504 into three light beams corresponding to RGB; a red color detector 524 for detecting red color light; a green color light detector 526 for detecting green color light; and a blue color light detector 528 for detecting blue color light as shown in FIG. 32.

The return light from the subject S enters the light guide 504 through the objective lens 502. The light beam projected from the light guide 504 is divided into three beams of red color light, green color light, and blue color light corresponding to RGB by a color decomposing prism 522. The divided beams of red color light, green color light, and blue color light reach the red color light detector 524, green color light detector 526, and blue color light detector 528, and are thus subject to photoelectrical conversion, respectively.

The light scanning optical device according to this modification acquires an RGB signal through one scanning of the subject, and thus, has higher dynamic resolution than image acquisition caused by sequentially emitting of the colored lights of RGB.

Figure 33:
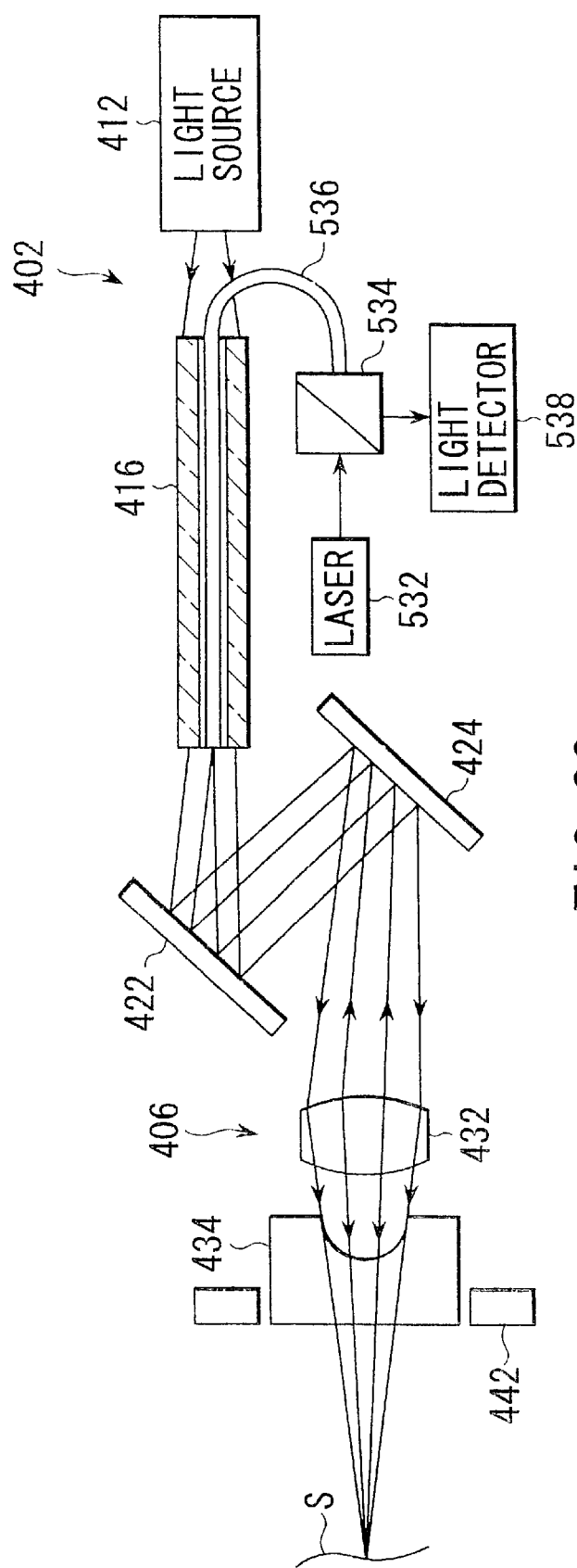
FIG. 33 schematically shows a light scanning optical device as a sixth modification of the light scanning optical device according to the second embodiment of the present invention that comprises a confocal optical system.

In a sixth modification of the light scanning optical device according to the second embodiment, as shown in FIG. 33, the light source section 402 comprises: a light source 412 for emitting light; and a hollow light guide 416 for acquiring the light from the light source 412 at one end and projecting the light beam at the other end. The light scanning optical device further comprises a confocal optical system.

Figure 34:
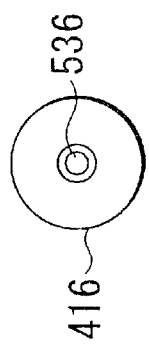
FIG. 34 shows an end face of the optical fiber and light guide optically disposed each other, as shown in FIG. 33.

The confocal optical system comprises an illumination laser 532; a beam splitter 534 for separating the forward light and the return light; an optical fiber 536 for guiding the forward light and the return light; and a light detector 538 for detecting the return light. The optical fiber 536 passes through a cavity extending the center of the light guide 416, as shown in FIG. 34, and is coaxially disposed relevant to the light guide 416. The optical fiber 536 is a single mode optical fiber, for example, and has an end face that functions as a pin hole. The optical fiber 536 may be a single mode optical fiber amplifier in order to improve light sensitivity of a confocal optical image.

In FIG. 33, the laser light beam projected from the illumination laser 532 passes through the beam splitter 534, and enters the optical fiber 536. The laser light beam projected from the end face of the optical fiber 536 is focused at a point by the converging optical system 406 via two one-dimensional scanning mirrors 422 and 424. A part of the light reflected or scattered at a point of the subject S positioned at the focused point returns back a forward path, enters the optical fiber 536 from the end face. Then, the part of light is directed to the light detector 538 by the beam splitter 534, and is subject to photoelectrical conversion by the light detector 538.

The end face of the optical fiber 536 functions as a pin hole. Thus, the light from points off a point conjugate to the end face of the optical fiber 536 does not reach the end face of the optical fiber 536. Therefore, while the laser light beam is scanned by two scanning mirrors 422 and 424, the return light is detected by the light detector 538, and a scanning signal and a detecting signal are processed all together, whereby a confocal image within the scanning range of the subject S is obtained.

On the other hand, the light emitted by the light source 412 enters the light guide 416 at one end, and is projected at the other end. The light beam projected from the light guide 416 is focused at the converging optical system 406 via the first scanning mirror 422 and the second scanning mirror 424. A part of the light reflected or scattered by the subject S is subject to photoelectrical conversion by a ring-shaped photodiode 442.

While light beam is scanned by two scanning mirrors 422 and 424, the return light is detected by the ring-shaped photodiode 442, and its output signal is processed together with a scanning signal, whereby a normal image within the scanning range of the subject S is obtained.

The light scanning optical device according to this modification comprises a confocal optical system, and can acquire a confocal image as well as such normal image within the scanning range of the subject S.

In a seventh modification of the light scanning optical device according to the second embodiment, as shown in FIG. 35, the scanning section 404 comprises: a first one-dimensional scanning prism 542 having a prism swingable about a first axis; and a second one-dimensional prism 544 having a prism swingable about a second axis that is not parallel to the first axis.

The first one-dimensional scanning prism 542 and the second one-dimensional scanning prism 544 have the same structures, each of which has a prism 552 supported by a pair of hinges 554 fixed to the fixed frame (not shown), as shown in FIG. 36. The prism 552 is swung about the axis that passes through the inside of the hinge 554 by a driving mechanism such as piezoelectric element.

The prism 552 has a pair of optical surfaces that is not parallel to each other, and its inclination direction, i.e., a direction in which an inclination between these surfaces is the greatest is parallel to a plane perpendicular to the swing axis. Therefore, the light beam that passes through the prism 552 is scanned in a plane perpendicular to the swing axis of the prism 552 according to the swinging of the prism 552.

The first one-dimensional scanning prism 542 and the second one-dimensional scanning prism 544 preferably have swing axes perpendicular to each other. For example, the first scanning prism 542, which has a swing axis vertical to the drawing, scans the light beam in a plane parallel to the drawing, and the second scanning prism 544 scans the light beam in a plane vertical to the drawing.

In FIG. 35, the light beam projected from the light guide 414 passes through the first one-dimensional scanning prism 542 and the second one-dimensional scanning prism 544 sequentially, and is focused by the converging optical system 406. A part of the light reflected or scattered by the subject S is subject to photoelectrical conversion by a ring-shaped photodiode 442.

While the light beam is scanned by two one-dimensional scanning prisms 542 and 544, the return light is detected by the ring-shaped photodiode 442, and its output signal is processed together with a scanning signal, whereby an image within the scanning range of the subject S is obtained.

According to the light scanning optical device according to this modification, the scanning section 404 has no reflection face, and thus, a loss of the light at the scanning section 405 is reduced.

In an eighth modification of the light scanning optical device according to the second embodiment, as shown in FIG. 37, the scanning section 404 comprises a two-dimensional scanning prism 560 having a prism swingable about a first axis and about a second axis that is not parallel to the first axis.

The two-dimensional scanning prism 560 has a so-called gimbal structure, as shown in FIG. 39. This scanning prism comprises: a prism 562; a first pair of hinges extending from the prism 562 to both sides along the first axis; a movable frame 566 for supporting a prism 562 via the first pair of hinges 564; a second pair of hinges 568 extending from the movable frame 566 to both ends along the second axis perpendicular to the first axis; and a fixing frame 570 for supporting the movable frame 566 via the second pair of hinges 568. The prism 562 can be swung about the axis passing through the inside of the first hinge 564, and swung about the second axis passing through the inside of the second hinge 568 together with the movable frame 566, by the driving mechanism such as piezoelectric element. Namely, the prism 562 can be swung about two axes perpendicular to each other.

The prism 562 has a pair of optical surfaces that is not parallel to each other. As shown in FIG. 38, its inclination direction, i.e., a direction in which an inclination between these surfaces is the greatest is not parallel to both of the plane perpendicular to the first axis passing through the inside of the first hinge 564 and the plane perpendicular to the second axis passing through the inside of the second hinge 568. Therefore, the swinging about the first axis of the prism 562 scans the optical beam that passes through the prism in a plane perpendicular to the first axis. The swinging about the second axis of the prism 562 scans the light beam passing through the prism in a plane perpendicular to the second axis. Namely, the two-dimensional scanning prism 560 can scan light beam in a two-dimensional manner.

In FIG. 37, the light beam projected from the light guide 414 passes through the two-dimensional scanning prism 560, and is focused by a converging optical system 406. A part of the light reflected or scattered by the subject S is subject to photo-electrical conversion by the ring-shaped photodiode 442. While light beam is scanned by the two-dimensional scanning prism 560, the return light is detected by the ring-shaped photodiode 442, and its output signal is processed together with a scanning signal, whereby an image within the scanning range of the subject S is obtained.

According to the light scanning optical device according to this modification, the scanning section 404 has no reflection face, and thus, a loss of the light at the scanning section 404 is reduced.

Figure 40:
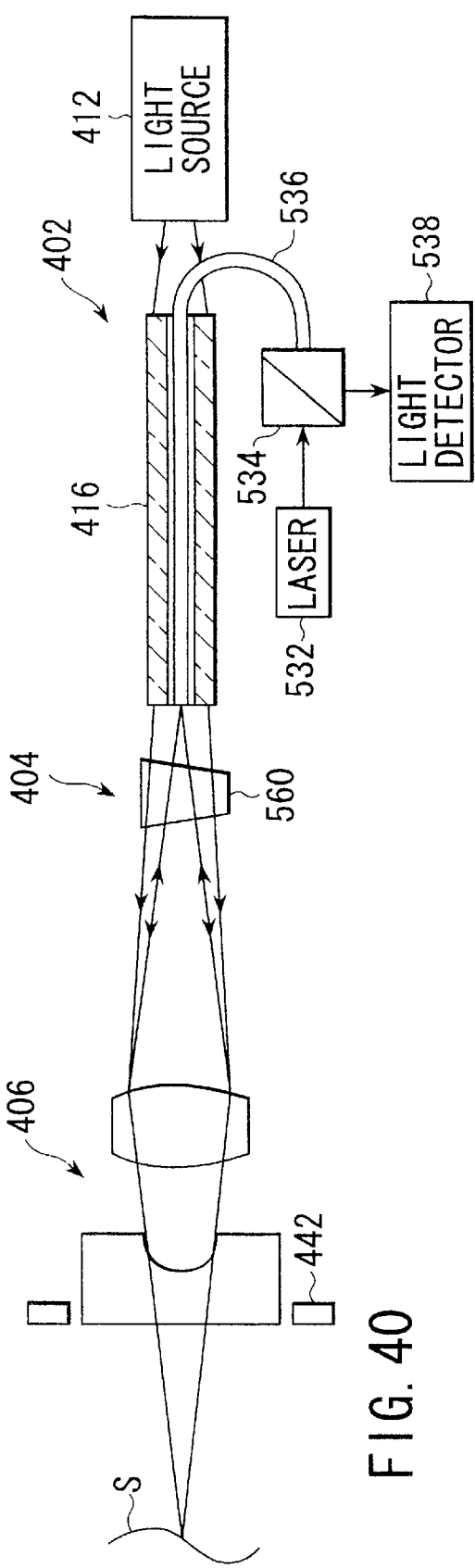
FIG. 40 schematically shows a light scanning optical device as a ninth modification of the optical scanning optical device according to the second embodiment of the present invention that comprises a confocal optical system.

In a ninth modification of the light scanning optical device according to the second embodiment, as shown in FIG. 40, a light source 402 comprises: a light source 412 for emitting light; and a hollow light guide 416 for collecting the light from the light source 412 at one end and projecting a light beam at the other end. The scanning section 404 comprises a two-dimensional scanning prism 560. The light scanning optical device further comprises a confocal optical system.

This confocal optical system comprises: an illumination laser 532; a beam splitter 534 for separating the forward light and the return light; an optical fiber 536 for guiding the forward light and the return light; and a light detector 538 for detecting the return light. The optical fiber 536 passes through a cavity extending the center of the light guide 416, and is disposed coaxially to the light guide 416. The optical fiber 536 is a single mode optical fiber, for example, and has an end face, which functions as a pin hole. The optical fiber 536 may be a single mode optical fiber amplifier in order to improve the light sensitivity of a confocal optical image.

The laser light beam projected from the illumination laser 532 passes through the beam splitter 534, and enters the optical fiber 536. The laser light beam projected from the end face of the optical fiber 536 is focused at a point by the converging optical system 406 through the two-dimensional scanning prism 560. A part of the light reflected or scattered at a point of the subject S positioned at the focused point returns back the forward path, and enters the optical fiber 536 from the end face. Then, the part of light propagates its inside, is directed to the light detector 538 by the beam splitter 534, and is subject to photoelectrical conversion by the light detector 438.

The end face of the optical fiber 536 functions as a pin hole. Thus, the light from a point that comes out of a confocal point relevant to the end face of the optical fiber 536 does not reach the end face of the optical fiber 536. Therefore, while laser light beam is scanned by the two-dimensional scanning prism 560, the return light is detected by the light detector 538, and a scanning signal and a detecting signal are processed all together, whereby a confocal image within the scanning range of the subject S is obtained.

On the other hand, the light emitted by the light source 412 enters the light guide 416 at one end, and is projected at the other end. The light beam projected from the converging optical system 416 is focused by the converging optical system 406 through the two-dimensional scanning prism 560. A part of the light reflected or scattered by the subject S is subject to photoelectrical conversion by a ring-shaped photodiode 442.

While light beam is scanned by the two-dimensional prism 560, the return light is detected by a ring-shaped photodiode 442, and its output signal is processed together with a scanning signal, whereby a normal image within the scanning range of the subject S is obtained.

The light scanning optical device according to this modification comprises a confocal optical system. Thus, a confocal image as well as normal image within the scanning region of the subject S is obtained.

Figure 41:
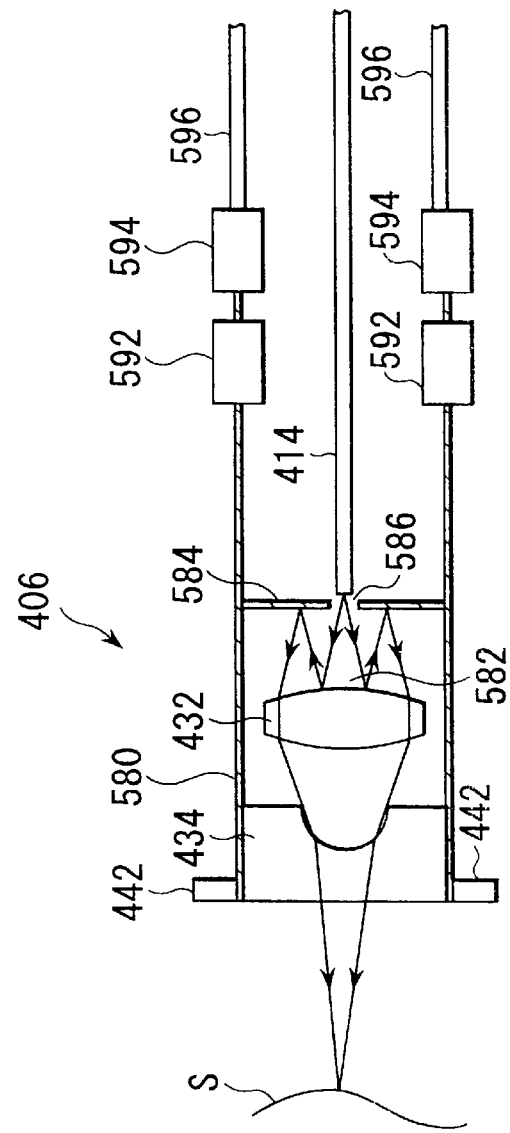
FIG. 41 schematically shows a scanning section and a converging optical system in a light scanning optical device as a tenth modification of the light scanning optical device according to the second embodiment of the present invention.

In a tenth modification of the light scanning optical device according to the second embodiment, as shown in FIG. 41, the converging optical system 406 comprises: a first fixed mirror 582 for returning an optical path of the light beam projected from the light guide 414; a second fixed mirror 584 for returning again an optical path of the light beam reflected by the first fixed mirror 582; and a lens system having a lens 432 and a lens 434. These optical elements are linearly arranged and fixed in one unit 580. The second fixed mirror 584 has at its center an opening 586, which allows the light beam projected from the light guide 414 to pass through.

The scanning section 404 comprises: a first one-dimensional drive piezoelectric vibrator that swings the unit 580 in a first direction in a one-dimensional manner; and a second one-dimensional drive piezoelectric vibrator 594 that swings the unit 580 in a second direction in a one-dimensional manner. These piezoelectric vibrators 592 and 594 are supported by a fixed support section 596.

For example, the first piezoelectric vibrator 592 swings the unit 580 in a direction parallel to the drawing, and the second piezoelectric vibrator 594 swings the unit 580 in a direction perpendicular to the drawing. In this manner, the unit 580 is swung in a two-dimensional manner, and therefore, light beam is scanned in a two-dimensional manner.

Therefore, while the unit 580 is swung in a two-dimensional manner, and light beam is scanned in a two-dimensional manner, the reflected or scattered light from the subject S is detected by a ring-shaped photodiode 442, and its detecting signal is processed together with a scanning signal, whereby an image within the scanning region of the subject S is obtained.

According to the light scanning optical device according to this modification, constituent elements of the converging optical system are linearly arranged, and thus, is advantageous in reducing the device in diameter. The first fixed mirror 582 and the second fixed mirror 584 may be omitted. Although the light scanning optical device in which the first fixed mirror 582 and the second fixed mirror 584 are eliminated requires a long inflexible portion relevant to application to an endoscope, this device is advantageous in improvement of the degraded efficiency of light utilization caused by reflection. In the light scanning optical device according to this modification, although all constituent elements of the converging optical system are swung, only a lens system comprising a lens 432 and a lens 434 may be swung.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light scanning optical device comprising:
   a light source simultaneously illuminating an entire imaging area of a subject;
   a converging optical system converging light returning from a specific minute region of the subject through a path different from a path of the illumination from the light source;
   a light detector detecting the light converged by the converging optical system; and
   a scanning mirror scanning the specific minute region, the scanning mirror being produced by a semiconductor manufacturing process.

2. A light scanning optical device according to claim 1, wherein the scanning mirror has a curved reflection face, and this scanning mirror is compatible with one element of the converging optical system.

3. A light scanning optical device according to claim 1, further comprising a relay optical system relaying a scanning region caused by the scanning mirror.

4. A light scanning optical device according to claim 1, further comprising an optical fiber guiding the light from the scanning mirror, wherein the light detector comprises a photomultiplier detecting the light transmitted by the optical fiber.

5. A light scanning optical device according to claim 1, further comprising a selecting device selecting only light of a specific wavelength from the return light.

6. A light scanning optical device according to claim 1, further comprising a confocal optical system, the confocal optical system comprising a laser light source, a single mode optical fiber having a subject side end disposed at a position conjugate to the subject, the converging optical system, and the scanning mirror.

7. A light scanning optical device according to claim 1, wherein the scanning mirror comprises a two-dimensional scanning mirror.

8. A light scanning optical device according to claim 7, wherein the two-dimensional scanning mirror returns an optical path of the return light from the converging optical system, and the light scanning optical device further comprises a fixed mirror returning again the optical path of the return light from the two-dimensional scanning mirror.

9. A light scanning optical device according to claim 8, wherein the two-dimensional scanning mirror has an opening, which allows the light returned by the fixed mirror to pass through, the converging optical system includes an imaging lens, and the two-dimensional scanning mirror and the fixed mirror cross an optical axis of the imaging lens, therefore, the imaging lens, two-dimensional scanning mirror, and fixed mirror are linearly arranged each other.

10. A light scanning optical device according to claim 1, wherein the scanning mirror comprises a first one-dimensional scanning mirror, which reflects an optical path of the return light from the converging optical system, and the light scanning optical device further comprises a second one-dimensional scanning mirror, which reflects again the optical path of the return light reflected by the first one-dimensional scanning mirror, such that the two one-dimensional scanning mirrors have swing axes not parallel to each other, so as to scan the minute region in a two-dimensional manner in cooperation with each other.

11. A light scanning optical device according to claim 10, wherein a converging-optical system includes an imaging lens, the first one-dimensional scanning mirror cross an optical axis of the imaging lens, and the second one-dimensional scanning mirror off the optical axis of the imaging lens, such that neither of the first one-dimensional scanning mirror and the second one-dimensional scanning mirror is vertical to the optical path of the return light.

12. A light scanning optical device according to claim 1, wherein the light scanning optical device is non-confocal.

13. A light scanning optical device comprising:
   illumination means for simultaneously illuminating an entire imaging area of a subject;
   converging means for converging light returning from a specific minute region of the subject through a path different from a path of the illumination from the light source;
   light detecting means for detecting the light converged by the converging means; and
   scanning means for scanning the minute region, the scanning means being produced by a semiconductor manufacturing process.

14. A light scanning optical device according to claim 13, wherein the light scanning optical device is non-confocal.

15. An endoscope comprising a light scanning optical device at a distal end, the light scanning optical device comprising a light source simultaneously illuminating an entire imaging area of a subject, a converging optical system converging light returning from a minute region of the subject through a path different from a path of the illumination from the light source, a light detector detecting the light converged by the converging optical system, and a scanning mirror scanning the minute region, the scanning mirror being produced by a semiconductor manufacturing process, such that a viewing direction of the light scanning optical device coincides with an insert direction of the endoscope.

16. A light scanning optical device according to claim 15, wherein the light scanning optical device is non-confocal.

17. A light scanning optical device comprising:
   a light source illuminating a subject;

a scanning mirror scanning the illumination light from the light source, the scanning mirror being produced by the semiconductor manufacturing process;

a converging optical system converging the illumination light from the light source; and a light detector detecting light returning from the subject through a path different from a path of the illumination light from the light source, the light detector being disposed so as to directly detect reflected light from an entire imaging area of the subject.

18. A light scanning optical device according to claim 17, further comprising a relay optical system relaying a scanning region caused by the scanning mirror.

19. A light scanning optical device according to claim 17, wherein the scanning mirror has a curved reflection face, and the scanning mirror is compatible with the converging optical system.

20. A light scanning optical device according to claim 17, further comprising a selecting device selecting only light of a specific wavelength from the return light.

21. A light scanning optical device according to claim 17, further comprising a confocal optical system, the confocal optical system comprising a laser light source, a single mode optical fiber having a subject side end disposed at a position conjugate to the subject, the converging optical system, and the scanning mirror.

22. A light scanning optical device according to claim 17, wherein the scanning mirror comprises a first one-dimensional scanning mirror, which returns an optical path of the return light from the converging optical system, and the light scanning optical device further comprises a second one-dimensional mirror, which returns again the optical path of the return light reflected by the first one-dimensional scanning mirror, such that the two one-dimensional scanning mirrors have swing axes not parallel to each other, so as to scan the minute region in a two-dimensional manner in cooperation with each other.

23. A light scanning optical device according to claim 22, wherein the converging optical system includes an imaging lens, a first one-dimensional scanning mirror cross an optical axis of the imaging lens, and a second one-dimensional scanning mirror off the axis of the imaging mirror, such that neither of the first one-dimensional scanning mirror and the second one-dimensional scanning mirror is vertical to the optical path of the return light.

24. A light scanning optical device according to claim 17, wherein the scanning mirror comprises a two-dimensional scanning mirror.

25. A light scanning optical device according to claim 24, wherein the two-dimensional scanning mirror returns the optical path of the return light from the converging optical system, and the light scanning optical device further comprises a fixed mirror returning again the optical path of the return light from the two-dimensional scanning mirror.

26. A light scanning optical device according to claim 25, wherein the two-dimensional scanning mirror has an opening, which allows the light returned by the fixed mirror to pass through, the converging optical system includes an imaging lens, and the two-dimensional scanning mirror and the fixed mirror cross an optical axis of the imaging lens, therefore, the imaging lens, two-dimensional scanning mirror, and fixed mirror are linearly arranged each other.

27. A light scanning optical device according to claim 17, wherein the light scanning optical device is non-confocal.

28. A light scanning optical device comprising:

illumination means for illuminating a subject;

scanning means for scanning illumination light from the illumination means, the scanning means being produced by a semiconductor manufacturing process;

converging means for converging the illumination light from the illumination means; and light detecting means for detecting light returning from the subject through a path different from a path of the illumination light from the light source, the light detector being disposed so as to directly detect reflected light from an entire imaging area of the subject.

29. A light scanning optical device according to claim 28, wherein the light scanning optical device is non-confocal.

30. An endoscope comprising a light scanning optical device at a distal end, the light scanning optical device comprising a light source illuminating a subject, a scanning mirror scanning illumination light from the light source, the scanning mirror being produced by a semiconductor manufacturing process, a converging optical system converging the illumination light from the light source, and a light detector detecting return light from the subject through a path different from a path of the illumination light from the light source, the light detector being located so as to directly detect reflected light from an entire imaging area of the subject, such that a viewing direction of the light scanning optical device coincides with an insert direction of the endoscope.

31. A light scanning optical device according to claim 30, wherein the light scanning optical device is non-confocal.

* * * * *